United States Patent
Ichigaya

(10) Patent No.: US 6,619,382 B1
(45) Date of Patent: Sep. 16, 2003

(54) SPACER FOR COOLING DEVICES

(75) Inventor: Hiroshi Ichigaya, Saitama (JP)

(73) Assignee: Seft Development Laboratory Co., Ltd., Saitama (JP)

( * ) Notice: Subject to any disclaimer, the term of this patent is extended or adjusted under 35 U.S.C. 154(b) by 0 days.

(21) Appl. No.: 09/914,359

(22) PCT Filed: Oct. 1, 1999

(86) PCT No.: PCT/JP99/05421

§ 371 (c)(1),
(2), (4) Date: Aug. 27, 2001

(87) PCT Pub. No.: WO01/24664

PCT Pub. Date: Apr. 12, 2001

(51) Int. Cl.$^7$ ................................................. F28F 7/00
(52) U.S. Cl. ....................... 165/80.3; 165/185; 165/48.1
(58) Field of Search ........................ 165/47, 907, 48.1, 165/185, 73, 74, 80.3; 454/184

(56) References Cited

U.S. PATENT DOCUMENTS

| | | | | |
|---|---|---|---|---|
| 2,214,344 A | * | 9/1940 | Paul ............................. | 165/47 |
| 4,037,751 A | * | 7/1977 | Miller et al. ................. | 220/9 R |
| 4,765,397 A | * | 8/1988 | Chrysler et al. ............. | 165/80.3 |
| 5,205,353 A | * | 4/1993 | Willemsen et al. .......... | 165/185 |
| 5,957,194 A | * | 9/1999 | Azar ............................. | 165/185 |
| 6,244,331 B1 | * | 6/2001 | Budelman ................... | 165/185 |
| 6,263,955 B1 | * | 7/2001 | Azar ............................. | 165/80.3 |

* cited by examiner

Primary Examiner—Henry Bennett
Assistant Examiner—Terrell McKinnon
(74) Attorney, Agent, or Firm—Rabin & Berdo, PC

(57) ABSTRACT

The present invention provides a cooling device aimed spacer capable of flowing a lot of gas even by a lower pressure. Such a cooling device aimed spacer is used to form a cooling flow passage of a cooling device. The "cooling device" is to cool a user's body by flowing, by blowing means, a gas through a substantially flat flow passage formed at that side of the cooling device which contacts with the user's body. The cooling device aimed spacer comprises: a plurality of column-shaped members 32a each having a length component in the thickness direction of the cooling flow passage, and a plurality of connecting members 33a for connecting the tip ends of the plurality of column-shaped members 32a. The plurality of column-shaped members 32a are integrally formed to become physically continuous via base member 35. Further, the width of each of the column-shaped members 32a along a direction perpendicular to the gas-flowing direction is in a range of 0.2 mm to 1 cm when viewed from the thickness direction of the cooling flow passage; and the column-shaped members 32a are formed at-a ratio of 0.1 to 25 pieces per 1 cm$^2$ when viewed from the thickness direction of the cooling flow passage.

5 Claims, 21 Drawing Sheets

(a)

(b)

(c)

(a)

(b)

(c)

(a)

(b)

(c)

(a)

(b)

(c)

(a)

(b)

(c)

(a)

(b)

(a)

(b)

(c)

(a)

(b)

(c)

(a)

(b)

SPACER FOR COOLING DEVICES

TECHNICAL FIELD

The present invention relates to cooling device aimed spacers to be used for cooling devices such as cooling bedclothes, cooling seat cushions, cooling mats, cooling chairs, cooling clothes, and cooling shoes, for flowing therethrough ambient air to thereby cool an object body.

BACKGROUND ART

As bedclothes for cooling an object body such as at a sleepless summer night, there have been proposed devices for directly cooling the body such as by causing cooled air to flow into a covering futon and/or pillow. For example, covering futons of air flow-through type are filled with coarse cotton materials, or three-dimensional fabrics, for example, so as to flow air through such fillers. Such cotton materials and three-dimensional fabrics act as spacers for flowing air therearound. Namely, members of the covering futon are overlapped with each other via space serving as a flow passage for air. In addition to the aforementioned cotton materials and three-dimensional fabrics, spacers to be used for cooling devices of air flow-through type include continuous-foam sponges and entwined hard fibers.

However, all of the aforementioned spacers only provide narrow gaps for passing air therethrough, thereby resulting in an extremely large viscous drag upon impingement of air onto respective members of the spacer. As such, in order to flow a lot of air through spacers so as to obtain a sufficient cooling effect, it is required to apply a higher pressure to the air. Thus, the conventional cooling devices of air flow-through types require devices for generating a high pressure, thereby resulting in an extra cost as well as various disadvantages due to the high pressure.

DISCLOSURE OF THE INVENTION

The present invention has been carried out in view of the conventional technique circumstances, and it is therefore an object of the present invention to provide a cooling device aimed spacer capable of allowing a lot of air to flow therethrough even by a lower pressure.

To achieve the aforementioned object, the first invention resides in a cooling device aimed spacer to be used in a cooling device which cools a cooling object by flowing, by blowing means, a gas through a substantially flat flow passage formed at.that side of the cooling device which contacts with the cooling object, in which the cooling device aimed spacer serves to form the flow passage and comprises: a plurality of plate-like projecting portions arranged parallel to the gas-flowing direction in a state where the plate-like projecting portions are upstanding in the thickness direction of the flow passage, wherein the plurality of plate-like projecting portions are integrally formed to become physically continuous such that: the width of each of the plate-like projecting portions along a direction perpendicular to the gas-flowing direction is in a range of 0.2 mm to 2 cm when viewed from the thickness direction of the flow passage; and the plate-like projecting portions are formed at a ratio of 0.2 to 5 pieces per 1 cm along the direction perpendicular to the gas-flowing direction when viewed from the thickness direction of the flow passage.

To achieve the above object, the second invention resides in a cooling device aimed spacer to be used in a cooling device which cools a cooling object by flowing, by blowing means, a gas through a substantially flat flow passage formed at that side of the cooling device which contacts with the cooling object, in which the cooling device aimed spacer serves to form the flow passage and comprises: a plurality of column-shaped members arranged in a state upstanding in the thickness direction of the flow passage, wherein the plurality of column-shaped members are integrally formed to become physically continuous such that: the width of each of the column-shaped members along a direction perpendicular to the gas-flowing direction is in a range of 0.2 mm to 1 cm when viewed from the thickness direction of the flow passage; and the column-shaped members are formed at a ratio of 0.1 to 25 pieces per 1 cm2 when viewed from the thickness direction of the flow passage.

To achieve the above object, the third invention resides in a cooling device aimed spacer to be used in a cooling device which cools a cooling object by flowing, by blowing means, a gas through a substantially flat flow passage formed at that side of the cooling device which contacts with the cooling object, in which the cooling device aimed spacer serves to form the flow passage and comprises: a plurality of column-shaped members each having a length component in the thickness direction of the flow passage, and a plurality of connecting members for connecting one ends of the plurality of column-shaped members, wherein the plurality of column-shaped members are integrally formed to become physically continuous such that: the width of each of the column-shaped members along a direction perpendicular to the gas-flowing direction is in a range of 0.2 mm to 1 cm when viewed from the thickness direction of the flow passage; and the column-shaped members are formed at a ratio of 0.1 to 25 pieces per 1 cm2 when viewed from the thickness direction of the flow passage.

BEST MODE FOR CARRYING OUT THE INVENTION

There will be described hereinafter the best mode for carrying out the present invention, with reference to the accompanying drawings.

The present inventors have invented cooling devices such as cooling bedclothes, cooling seat cushions, cooling mats, cooling chairs, cooling clothes, and cooling shoes, which provide a sufficient cooling effect with a simple structure and without deteriorating the health of a user. Each of these cooling devices will cool an object body, such as a user's body, by flowing a gas such as air using an electromotive fan through a cooling flow passage provided at a portion of the device which contacts the object body. Such a cooling device has an aimed spacer so as to form the cooling flow passage.

The aforementioned cooling devices are generally classified into two types, i.e., an air flow-through type and a vaporization heat utilizing type. In cooling devices of the air flow-through type, ambient air which is cooler than a user's body temperature is flowed into a cooling flow passage from one end thereof using a fan, and flowed out of the other end of the cooling flow passage, to thereby increase a temperature gradient between the body and the cooling flow passage. The value of such a temperature gradient determines the amount of heat to be radiated from the user's body, to thereby largely affect the comfort of the user. As such, it is possible to cause the user to feel cool, by forcibly increasing the temperature gradient near the body surface to thereby increase the amount of heat to be radiated therefrom. Typically, the cooling flow passage is covered by a cloth sheet.

Figure 1:
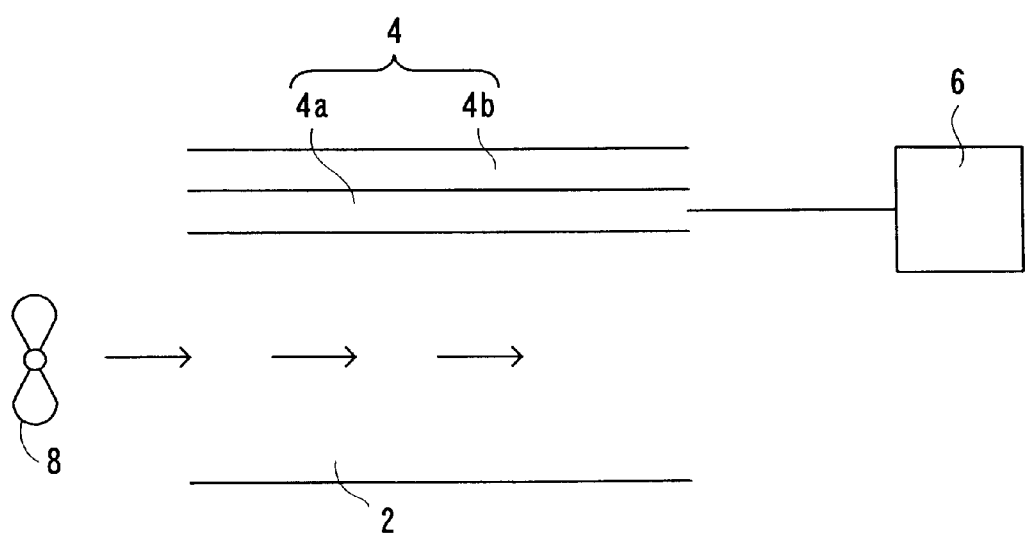
FIG. 1 is a schematic constitutional view of a cooling device of a vaporization heat utilizing type.

FIG. 1 is a schematic constitutional view of a cooling device of a vaporization heat utilizing type. As shown in FIG. 1, the cooling device of the vaporization heat utilizing type is provided with a cooling flow passage 2, and an evaporation sheet 4 arranged at that side of the cooling flow passage 2 which contacts with an object body. Such an evaporation sheet 4 includes a water conducting member 4a for conducting water, and a waterproof member 4b for repelling the water infiltrated into the water conducting member 4a. This evaporation sheet 4 is arranged such that the water conducting member 4a is opposed to the cooling flow passage 2. Further, the water conducting member 4a is supplied with water from a tank 6, and the cooling flow passage 2 is supplied with air by a fan 8, so that the water is evaporated from the water conducting member 4a and so that the latent heat of the water resulting from such evaporation is provided by absorption of much heat from the body through the waterproof member 4b, to thereby cool the body.

Both of the aforementioned types of cooling devices obtain cooling effects by flowing air through a substantially flat cooling flow passage, to thereby efficiently take away heat from the body so as to obtain the cooling effect. As such, the cooling effect is determined by as to what structure is to be adopted as the cooling device aimed spacer for ensuring such a cooling flow passage. Thus, the cooling device aimed spacer is particularly important among the constituent elements of a cooling device.

Actually, it is possible to improve a cooling effect of a cooling device, by increasing an air flow quantity per unit time to be flowed through the cooling flow passage. Conversely, in case of a constant flow quantity, higher flow speeds of air near a body surface allow higher cooling effects. To this end, it is advantageous to sufficiently reduce the thickness of the cooling device aimed spacer. However, the reduced thickness of the cooling device aimed spacer for improving the flow speed leads to an increased pressure required for flowing air into the cooling flow passage, mainly in relation to the viscosity of air.

Figure 2:
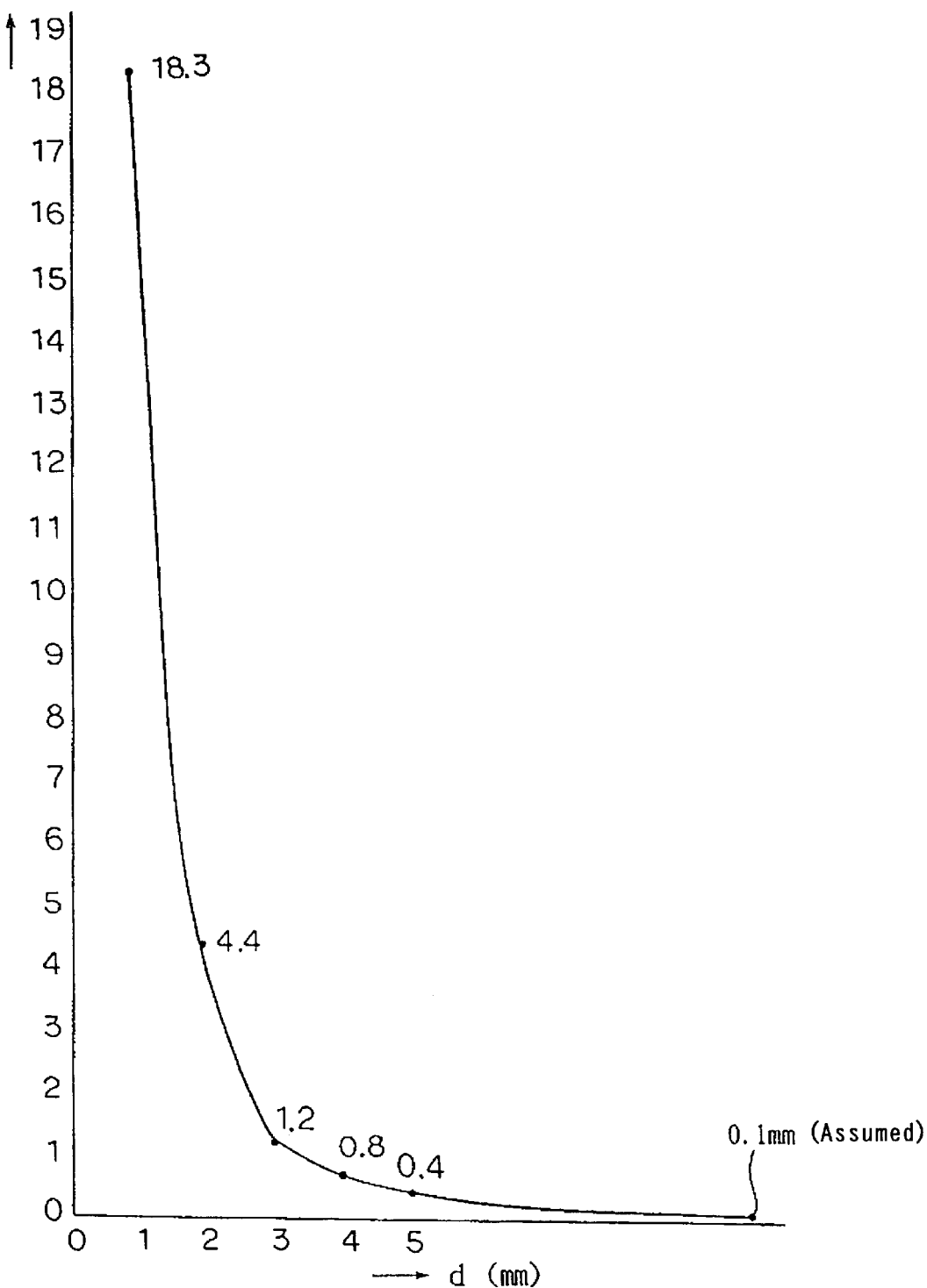
FIG. 2 a graph showing a result of a preliminary experiment for checking a relationship between a cooling flow passage gap and a pressure under a constant air flow quantity.

There will be now explained a preliminary experiment conducted by the present inventors for the relationship between a thickness of a cooling flow passage and a difference between an inlet pressure and an outlet pressure of the cooling flow passage. In this preliminary experiment, two aluminum plates of 500 mm length and 250 mm width were disposed parallel to each other, both ends in the longitudinal direction were opened, and both side ends were air-tightly closed, to thereby prepare a cooling flow passage. Further, there was studied as to how the difference between the inlet pressure and outlet pressure of the cooling flow passage was changed, when air was supplied in the longitudinal direction at a flow rate of 1 liter/sec by an electromotive fan while changing the distance between the aluminum plates. FIG. 2 is a graph showing the result of the preliminary experiment. In FIG. 2, the abscissa represents the distance d [mm] between the two aluminum plates, and the ordinate represents the pressure difference p [mmH$_2$O]. Here, the pressure unit [mmH$_2$O] has a relationship with a unit of atm such that 1 mmH$_2$O=9.672×10$^{-5}$ atm.

Since the amount of blown air is fixed, the smaller the distance d, the larger the flow rate of air. As the flow rate becomes large, the resistance to which the flowing air is subject becomes large due to the friction between the viscous air and the inner wall of the passage. As such, when the thickness of the cooling flow passage is reduced to increase the flow rate, the required pressure is rapidly increased as shown in FIG. 2. Pressures exceeding a certain level require not a small-sized fan but a specific fan, thereby resulting in an excessive cost, larger electric power consumption, and an unnegligible noise problem of the fan. Thus, the cooling device having such a structure can not be applied to bedclothes. Further, excessively higher pressures of air lead to problems of increased leakage of air such as at a joint portion between the cooling flow passage and the flow inlet, and of increased leakage of air from the sheet contacting with the cooling device aimed spacer forming the cooling flow passage. Under these circumstances, it is impractical to reduce the thickness of the cooling flow passage, and of the cooling device aimed spacer, down to a value smaller than 2 mm.

On the other hand, excessively increased thickness of the cooling flow passage so as to increase the flow quantity deteriorates the cooling effect, and requires an increased strength of the cooling device aimed spacer to be used for forming the cooling flow passage. Thus, the practical upper limit of the thickness of the cooling flow passage appears to be on the order of 20 to 30 mm, depending on the type of the cooling device.

Further, the cooling device aimed spacer is required to have a certain degree of flexibility, since the cooling flow passage in the cooling device is contact with a user's body. Moreover, the cooling device aimed spacer is required to be sufficiently lightweight when used as a cooling device to cover futons, whereas the cooling device aimed spacer is required to have a sufficient strength for supporting the weight of the user's body such as when used as a cooling device to an underlying futon.

There will be explained hereinafter structural features of the cooling device aimed spacers according to the present invention.

Each of the cooling device aimed spacers of the present invention is provided to form a cooling flow passage of a cooling device, and is formed with a plurality of projecting portions arranged to be substantially flat. Herein, the cooling device aimed spacers are generally classified into three types of A, B and C. Each of the spacers of the type A utilizes a plurality of plate-like projecting portions arranged parallel to the gas-flowing direction in a state where the plate-like projecting portions are upstanding in the thickness direction of the cooling flow passage. Namely, each of the spacers of the type A previously defines the gas-flowing direction. Those spacers of the Embodiments 1 and 2 to be described later correspond to this type A.

The spacer of the type B utilizes, as projecting portions, a plurality of column-shaped members regularly arranged in a state upstanding in the thickness direction of the cooling flow passage. The spacer shown in the Embodiment 3 to be described later corresponds to this type B. Further, each of the spacers of the type C is provided with: a plurality of column-shaped members having length components along the thickness direction of the cooling flow passage; and a plurality of connecting members for connecting the tip ends of the column-shaped members. In this case, one projecting portion is constituted of one connecting member and pertinent column-shaped members connected by the one connecting member. Those spacers shown in the Embodiments 4 and 5 to be described later correspond to this type C.

Actually, each of such cooling device aimed spacers is constituted such that projecting portions are integrally formed to become physically continuous via a base member. This is because, independently or separately forming projecting portions requires a laborious work in manufacturing spacers, and is thus impractical. However, the cooling device aimed spacer to be used for forming the cooling flow passage need not be integral as a whole. For example, it is possible to use the spacer by dividing it into a plurality of segments, or to use duly arranged smaller 5-cm square spacers.

Concretely, such cooling device aimed spacers can be inexpensively manufactured such as by injection molding of soft plastics. Namely, the spacers are formed by pouring heated and fluidized plastics into a mold. In this way, since the cooling device aimed spacer is integrally formed by using a mold, the cooling device aimed spacer has no portions which overlap with other portions of the spacer via space in the thickness direction of the spacer upon such integral forming. However, such as when a reinforcing member is attached to the cooling device aimed spacer after the integral formation, there may be formed a portion overlapping with other portions of the spacer via space in the thickness direction of the spacer. It is of course possible to do so.

The cooling device aimed spacer of this embodiment has a thickness of at least 2 mm, in view of the result of the aforementioned preliminary experiment. This is because, a thickness smaller than 2 mm requires a considerably increased air pressure so as to flow air at a constant flow quantity, and is thus impractical.

In such cooling device aimed spacers, how the allocation density of projecting portions and the distances therebetween are to be designed shall be determined in consideration of the strength of the material, the shape of the projecting portions, and the applicable kind of cooling device. In this case, the particularly important point is to reduce the viscous drag upon impingement of air onto the projecting portions. This is because, larger viscous drags require a specific fan for generating larger pressures so as to flow air at a constant flow quantity, to thereby cause further problems of increased electric power consumption and noises. The results of the experiment conducted by the present inventors have shown a considerable increase of viscous drag, in case of flowing a practical amount of blown air (such as 1 liter/sec for a spacer having a width of 250 mm and a thickness of 5 mm), while adopting a value less than 2 mm as a distance between projecting portions themselves in the type A and as a distance between column-shaped members themselves in the types B and C. Thus, it is required to adopt a value of at least 2 mm as a distance between projecting portions themselves in the type A and as a distance between column-shaped members themselves in the types B and C. In other words, this requires that: in the spacer of the type A, the number of projecting portions per 1 cm along a direction perpendicular to the gas-flowing direction should be 5 at the utmost when viewed from the thickness direction of the spacer; and in the spacer of the type B or C, the number of column-shaped members per 1 $cm^2$ should be 25 at the utmost when viewed from the thickness direction of the spacer.

Further, since the cooling device aimed spacers also have a purpose to flow air therethrough, it is also necessary to increase an opening ratio within a plane perpendicular to the air-flowing direction to a certain extent. Concretely, it is preferable to set such an opening ratio at 30% or more. In this respect, even an opening ratio of 99% leads to a considerably increased viscous drag, if the ratio is provided by arranging fibers of 10 microns at a pitch of as narrow as 1 mm. As such, the opening ratio should be duly increased, after satisfying the aforementioned requirement of the distance between the projecting portions or between column-shaped members. Considering the above, these embodiments provide that: in the spacer of the type A, the width of each of the plate-like projecting portions along the direction perpendicular to the gas-flowing direction is set at 0.2 mm to 2 cm when viewed from the thickness direction of the spacer; and in the spacer of the type B, C, the width of each of column-shaped members along the direction perpendicular to the gas-flowing direction is set at 0.2 mm to 1 cm when viewed from the thickness direction of the spacer. Note, the widths narrower than 0.2 mm in the spacer of the type B, C lead to a considerably reduced strength of the column-shaped member and lead to failure of forming thereof by a mold.

Meanwhile, from various aspects, it is also preferable that the opening ratio is large at that side of the cooling device aimed spacer which contacts with the user's body. Concretely, such an opening ratio is preferably 20% or more. Specifically, cooling devices of the air flow-through type inherently have such a secondary effect that the moisture near the body surface due to perspiration from the body surface can be discharged into the cooling flow passage. However, such a secondary effect can be hardly expected due to less permeation of water vapor through the spacer, if the opening ratio is small at the user's body contacting side of the spacer when an air-tight material is used for the spacer. Further, in the cooling device of the vaporization heat utilizing type, smaller opening ratios at the user's body contacting side of the spacer necessarily lead to a smaller contact ratio of the flowing air with the evaporation sheet, to thereby reduce the evaporation amount which results in a deteriorated cooling effect.

In each of the aforementioned two types of cooling devices, the cooling flow passage is formed by covering a cloth sheet or evaporation sheet onto a body contacting side of the cooling device aimed spacer. Thus, in applying the cooling device such as to an underlying futon, wider distances between projecting portions of the cooling device aimed spacer result in a rugged feeling by the projecting portions when a user's body is placed on the projecting portions. To restrict such a rugged feeling, it is enough to interpose a meshed material as an insertion material between the sheet and the column-shaped members or connecting members. However, the effect by virtue of such a meshed material is limited, if the distance between projecting portions is so wide. Thus, to effectively restrict the rugged feeling, it is necessary to restrict the upper limit of the distance between projecting portions themselves. Concretely, it is preferable to set the distance between projecting portions themselves at 50 mm at the utmost in the type A, and the distance between column-shaped members themselves at 30 mm at the utmost in the type B. C. In view of the above, these embodiments provide that: in the spacer of the type A, the number of projecting portions per 1 cm along a direction perpendicular to the gas-flowing direction is set at at least 0.2 when viewed from the thickness direction of the cooling flow passage; and in the spacer of the Type B or C, the number of column-shaped members per 1 $cm^2$ is set at at least 0.1 when viewed from the thickness direction of the cooling flow passage.

There will be hereinafter described concrete embodiments of the cooling device aimed spacers according to the present invention.

FIGS. 3 through 16 are views for explaining various cooling device aimed spacers. In FIGS. 3 through 15, there are shown small pieces of cooling device aimed spacers such as 5 cm×4 cm.

Embodiment 1

FIG. 3(a), FIG. 3(b) and FIG. 3(c) are a schematic plan view, a schematic side view and a schematic partial perspective view of a cooling device aimed spacer 10a of an Embodiment 1, respectively.

Figure 3:
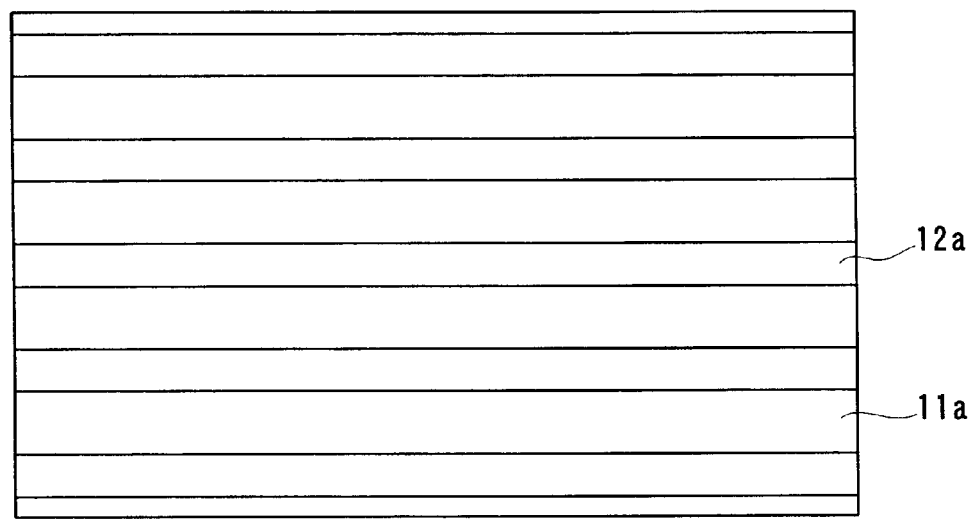
FIG. 3(*a*), FIG. 3(*b*) and FIG. 3(*c*) are a schematic plan view, a schematic side view and a schematic partial perspective view of a spacer according to an Embodiment 1 of the present invention, respectively.
Figure 3:
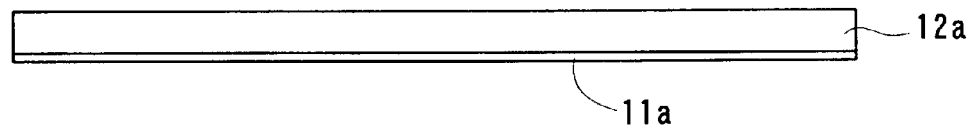
Figure 3:
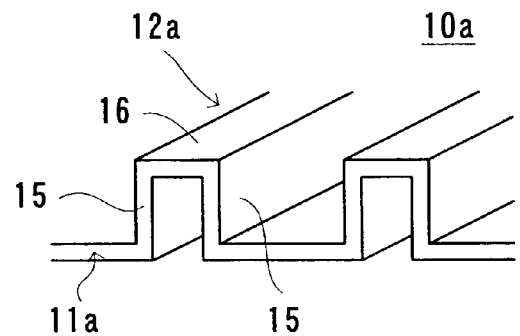

The cooling device aimed spacer 10a shown in FIG. 3 is called "hollow rail type", which includes a rectangular base member 11a and a plurality of rail-shaped projecting portions 12a. The plurality of rail-shaped projecting portions 12a are arranged such that the longitudinal direction of the rail-shaped projecting portions 12a are parallel to the long side of the base member 11a, and the plurality of rail-shaped projecting portions 12a are physically joined to be continuous via the base member 11a. As shown in FIG. 3(c), each of rail-shaped projecting portions 12a comprises two pieces of plate-like projecting portions 15, 15 and a connecting member 16 connecting the upper ends of the plate-like projecting portions 15, 15. Thus, there are formed passages for flowing air therethrough, by the space between adjacent rail-shaped projecting portions 12a and by the space within each rail-shaped projecting portion 12a.

The width of each of the plurality of plate-like projecting portions 15 along the direction perpendicular to the gas-flowing direction is set at 0.2 mm to 2 cm when viewed from the thickness direction of the spacer. Further, the-distance between the plurality of plate-like projecting portions 15 themselves is set at 2 mm to 50 mm, for example. Thus, the number of plate-like projecting portions 15 per 1 cm along a direction perpendicular to the gas-flowing direction is set at 0.2 to 5 inclusive when viewed from the thickness direction of the spacer. This is also true in the example 2 to be described later.

The hollow rail type of the cooling device aimed spacer 10a can be formed by bending a sheet material such as hard paper or by vacuum molding of a plastic film. Since the cooling device aimed spacer 10a is integrally formed in such a way, the cooling device aimed spacer 10a has no portions which overlap with other portions of the spacer via space in the thickness direction of the spacer. This is also true in the embodiments to be described later.

The spacer 10a of the Embodiment 1 can be readily manufactured and allows air to flow through not only the space between rail-shaped projecting portions 12a themselves but also the space within the rail-shaped projecting portion 12a. However, it is desirable to provide a meshed member as an insertion material on the rail-shaped projecting portions 12a, since the spacer 10a brings about a rugged feeling when used to form cooling flow passages of a cooling device. Further, since the spacer 10a has less flexibility in the longitudinal direction, it is desirable to apply the spacer 10a to a cooling device which does not require flexibility in such a direction.

Figure 4:
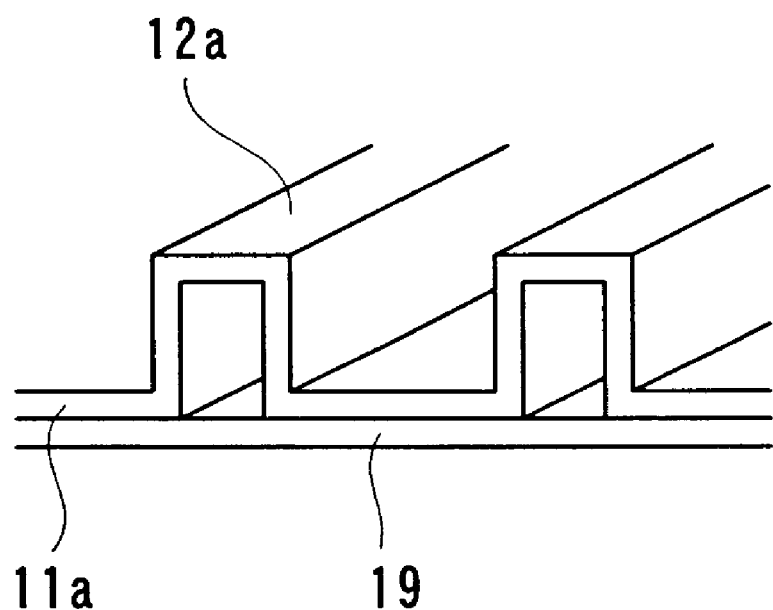
FIG. 4 is an enlarged schematic perspective view showing a modified embodiment of the spacer of the Embodiment 1.

Note, when it is required to increase the strength of the spacer 10a, it is possible to adhere a bottom plate 19 to the underside of the base member 11a as shown in FIG. 4.

Embodiment 2

FIG. 5(a), FIG. 5(b) and FIG. 5(c) are a schematic plan view, a schematic side view and a schematic partial perspective view of a cooling device aimed spacer lob according to an Embodiment 2, respectively.

Figure 5:
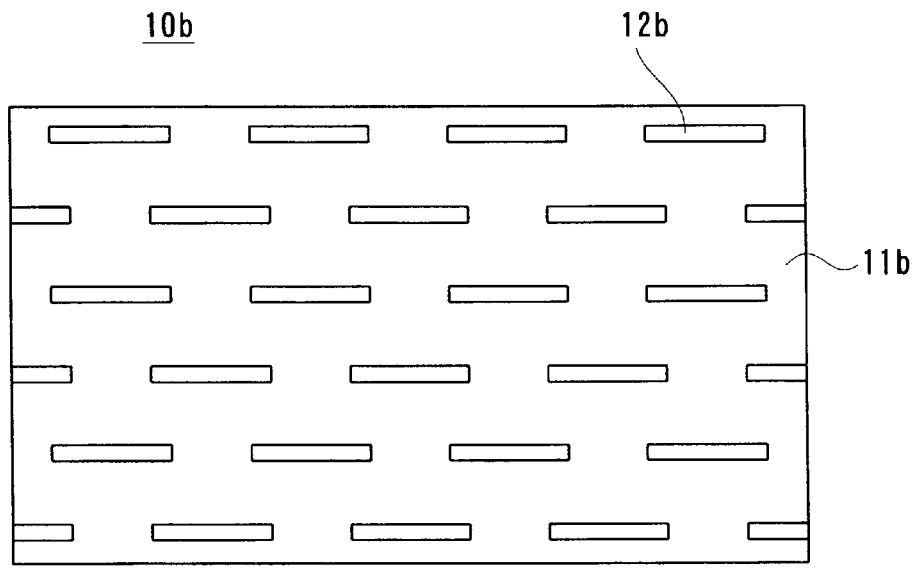
FIG. 5(*a*), FIG. 5(*b*) and FIG. 5(*c*) are a schematic plan view, a schematic side view and a schematic partial perspective view of a spacer according to an Embodiment 2 of the present invention, respectively.
Figure 5:
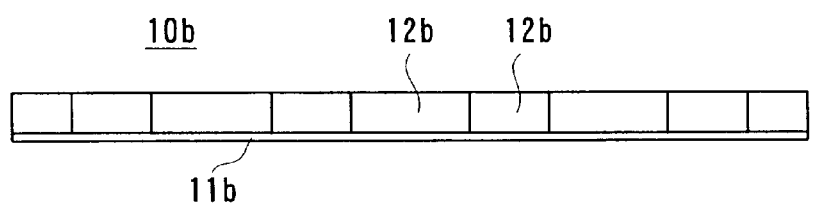
Figure 5:
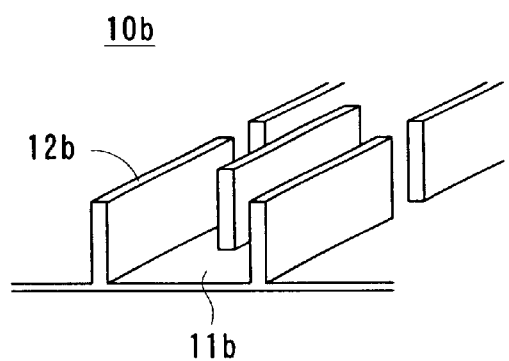

The cooling device aimed spacer lob shown in FIG. 5 is called a "rail division type", and includes a rectangular base member lib and a plurality of short plate-like projecting portions 12b. The plurality of plate-like projecting portions 12b are arranged such that the longitudinal direction of the plate-like projecting portions 12b are parallel to the long side of the base member 11b, and the plurality of plate-like projecting portions 12b are physically joined to be continuous via the base member 11b. The plate-like projecting portion 12b is short as compared with the plate-like projecting portion of the Embodiment 1, and can be regarded as being obtained by dividing the plate-like projecting portion of the Embodiment 1 into a plurality of segments. Unlike the Embodiment 1, the upper ends of the adjacent plate-like projecting portions 12b are not connected in the Embodiment 2, so that the space between adjacent plate-like projecting portions 12b acts as a passage for flowing air therethrough.

This rail division type of cooling device aimed spacer 10b can be formed by compression molding of rubber, or injection molding of soft plastics.

The spacer 10b of the Embodiment 2 is formed with a lot of short plate-like projecting portions 12b along the longitudinal direction of the spacer 10b, so that the spacer 10b has flexibility also in the longitudinal direction thereof. Further, this spacer 10b is capable of supporting a heavier load as compared with the spacer of the Embodiment 1.

It is desirable to provide a meshed member as an insertion material on the plate-like projecting portions 12b, since the spacer 10b brings about a rugged feeling when used to form cooling flow passages of a cooling device.

In the spacer 10b of the Embodiment 2, it is possible to increase the thickness of the plate-like projecting portion 12b to provide a cavity within it. This allows a lightweight spacer to be realized, considering its weight resistance. In this situation, the spacer 10b can be formed such as by compression molding of rubber, injection molding of soft plastics, or vacuum molding of plastic film.

Embodiment 3

FIG. 6(a), FIG. 6(b) and FIG. 6(c) are a schematic plan view, a schematic side view and a schematic partial perspective view of a cooling device aimed spacer 20 according to an Embodiment 3, respectively.

Figure 6:
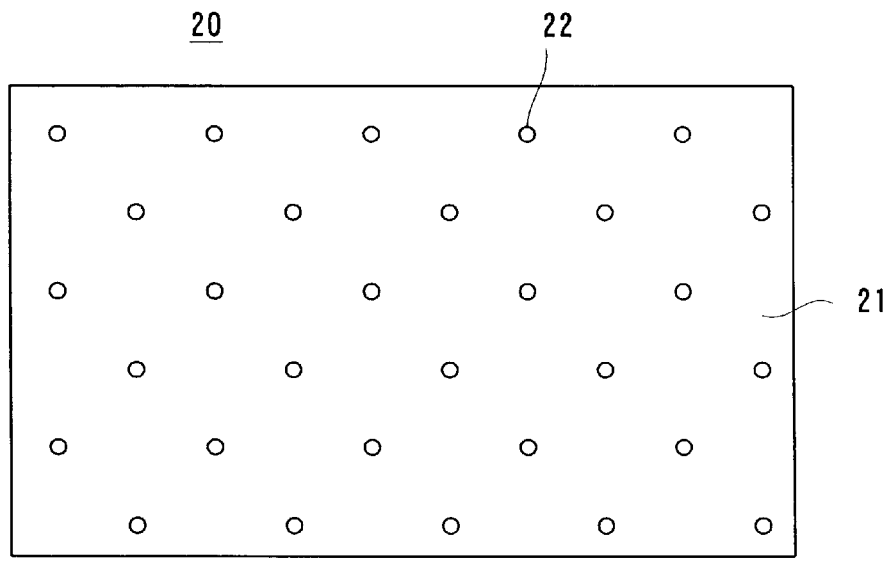
FIG. 6(*a*), FIG. 6(*b*) and FIG. 6(*c*) are a schematic plan view, a schematic side view and a schematic partial perspective view of a spacer according to an Embodiment 3 of the present invention, respectively.
Figure 6:
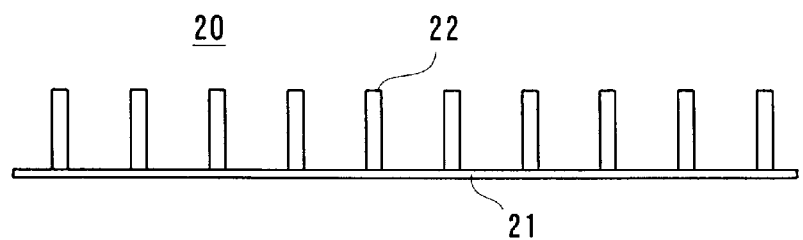
Figure 6:
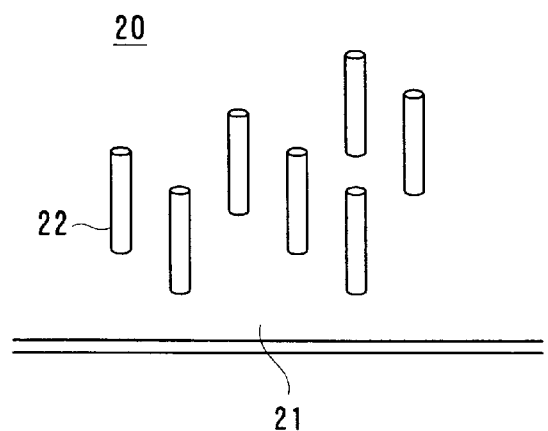

The cooling device aimed spacer 20 shown in FIG. 6 is called a "column-shaped type", and includes a rectangular base member 21 and a plurality of column-shaped members 22. Each of the column-shaped members 22 is formed to be vertically upwardly extended from the base member 21. Thus, the plurality of column-shaped members 22 are physically joined to be continuous via base member 21.

The width of each of the plurality of column-shaped members 22 along the direction perpendicular to the gas-flowing direction is set at 0.2 mm to 1 cm when viewed from the thickness direction of the spacer. Further, the distance between the column-shaped members 22 themselves is set at 2 mm to 30 mm, for example. Thus, the number of column-shaped members 22 per 1 $cm^2$ is 0.1 to 25 when viewed from the thickness direction of the spacer.

This column-shaped type of spacer 20 can be formed such as by compression molding of rubber, injection molding of soft plastics, or calendering method.

The spacer 20 of the Embodiment 3 has such advantages that this spacer 20 is lightweight, flexible in an omnidirectional manner, and capable of allowing air to pass through the spacer 20 in an omnidirectional manner. However, this spacer 20 is incapable of bearing a heavier load, and thus is suitable to be used for a cooling device, such as for clothes and covering futon. Note, it is possible to increase the diameter of the column-shaped member 22 to provide a cavity within it.

Embodiment 4

All of nine types of cooling device aimed spacers 30a, 30b, . . . , 30i shown in FIGS. 7 through 15 are so-called "member-connection types". Each of FIGS. 7 through 15, (a), (b) and (c) are a schematic plan view, a schematic side view of an applicable member-connection type spacer, and a schematic perspective view of a projecting portion of the spacer, respectively.

Figure 7:
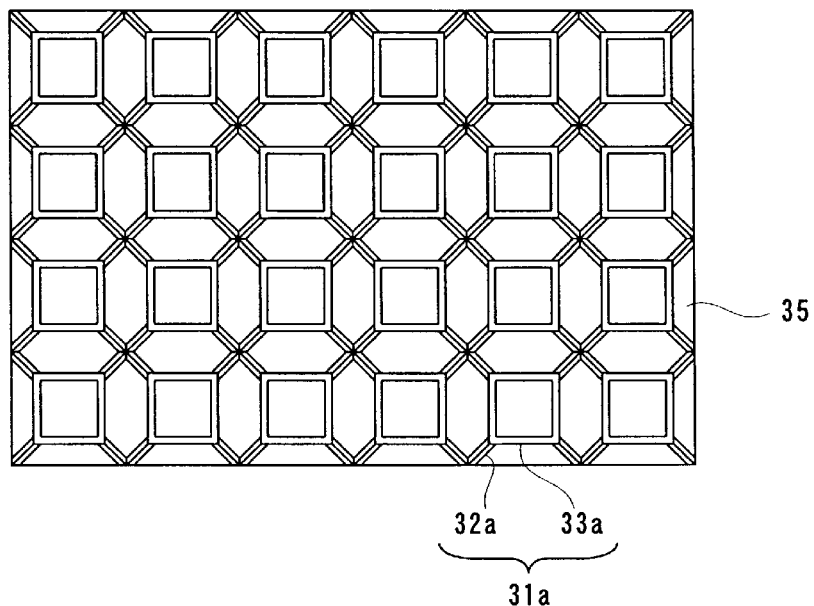
FIG. 7(*a*), FIG. 7(*b*) and FIG. 7(*c*) are a schematic plan view, a schematic side view of an example of a spacer according to an Embodiment 4 of the present invention, and a schematic perspective view of a projecting portion of the spacer, respectively.
Figure 7:
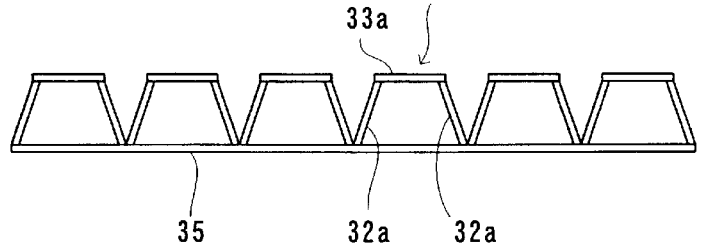
Figure 7:
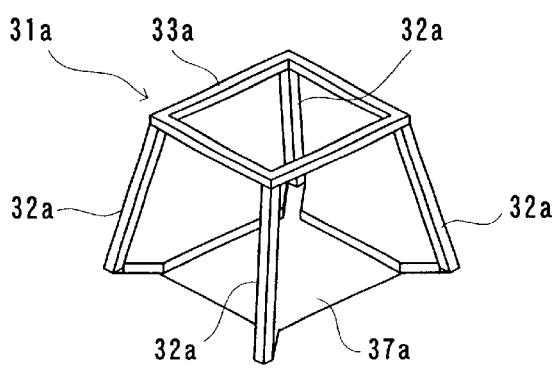

The member-connection type spacer 30a shown in FIG. 7 includes a plurality of projecting portions 31a substantially flatly arranged on a rectangular base member 35. Namely, the projecting portions 31a are physically joined to become continuous via base member 35. As shown in FIG. 7(c), each projecting portion 31a comprises four column-shaped members 32a and a square frame-shaped connecting member 33a. Each column-shaped member 32a is drawn obliquely upwardly from the base member 35. Each column-shaped member 32a has its tip end connected to one of the corners of the connecting member 33a. Further, each column-shaped member 32a of each pertinent projecting portion 31a has a lower end connected to lower ends of column-shaped members 32a of three projecting portions 31a adjacent to the pertinent projecting portion 31a, so that all projecting portions 31a are arranged regularly.

Figure 8:
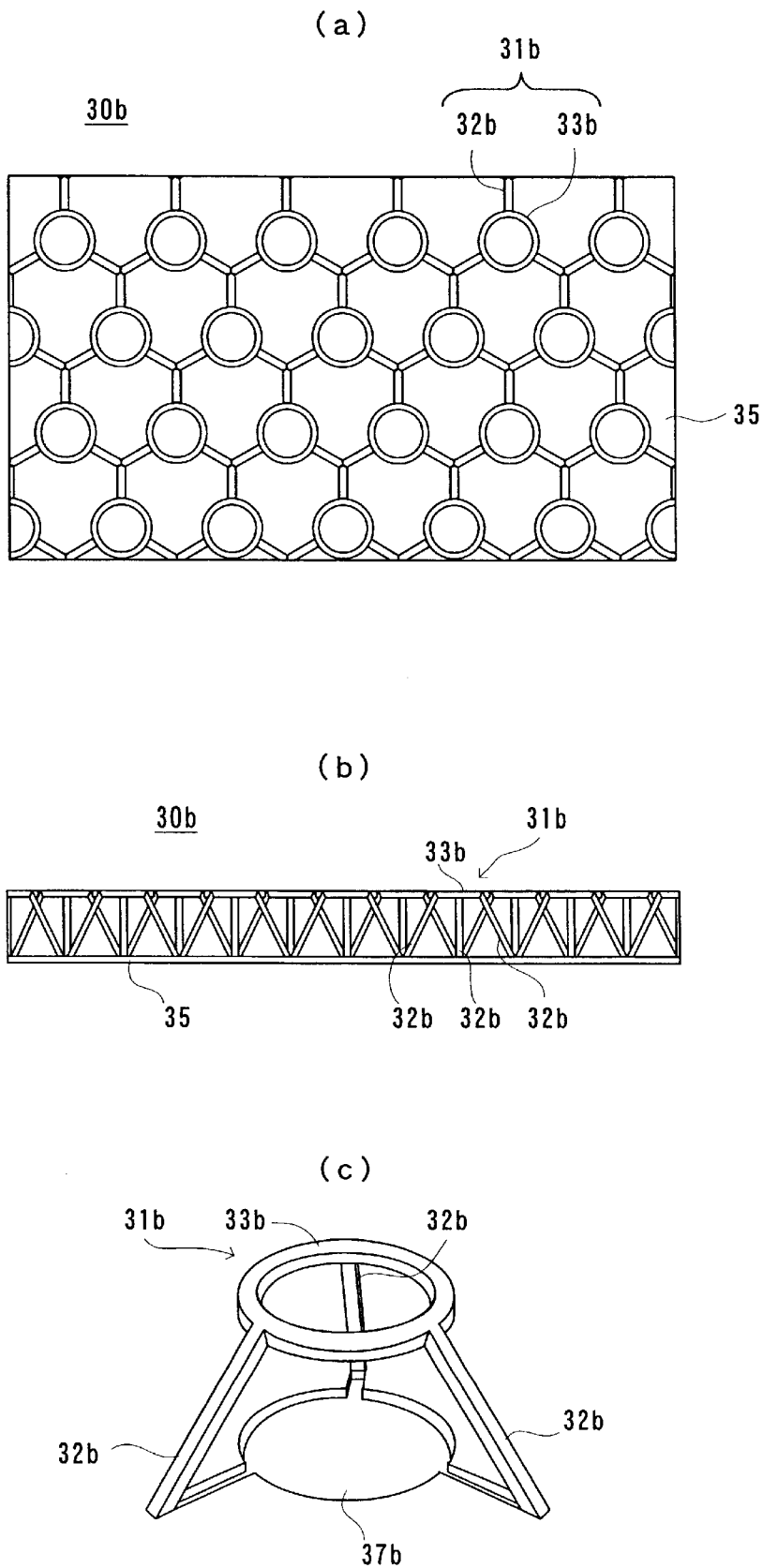
FIG. 8(*a*), FIG. 8(*b*) and FIG. 8(*c*) are a schematic plan view, a schematic side view of another example of a spacer according to an Embodiment 4 of the present invention, and a schematic perspective view of a projecting portion of the spacer, respectively.

The member-connection type spacer 30b shown in FIG. 8 includes a plurality of projecting portions 31b substantially flatly arranged on a rectangular base member 35. Namely, the projecting portions 31b are physically joined to be continuous via base member 35. As shown in FIG. 8(c), each projecting portion 31b comprises three column-shaped members 32b and a ring-shaped connecting member 33b. Each column-shaped member 32b is drawn obliquely upwardly from the base member 35. The tip ends of column-shaped members 32b are connected to the connecting member 33b. In this case, adjacent two column-shaped members 32b form an angle of 120° therebetween when viewed from the above of the spacer 30b as shown in FIG. 8(a). Further, each column-shaped member 32b of each pertinent projecting portion 31b has a lower end connected to lower ends of column-shaped members 32b of two projecting portions 31b adjacent to the pertinent projecting portion 31b. Thus, all projecting portions 31b are arranged regularly, and present a substantially honeycomb pattern when viewed from the above.

Figure 9:
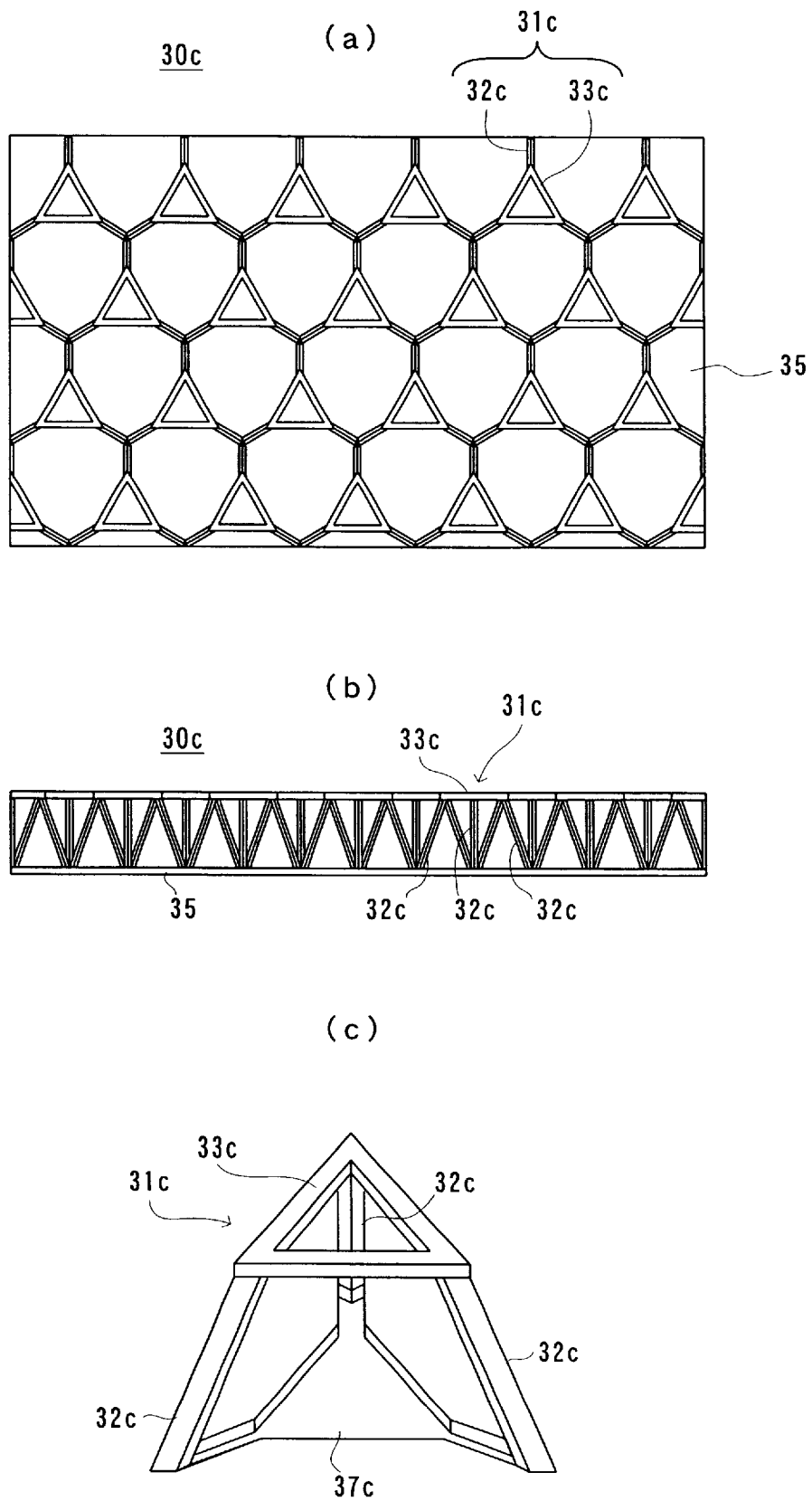
FIG. 9(a), FIG. 9(b) and FIG. 9(c) are a schematic plan view, a schematic side view of yet another example of a spacer according to an Embodiment 4 of the present invention, and a schematic perspective view of a projecting portion of the spacer, respectively.
Figure 10:
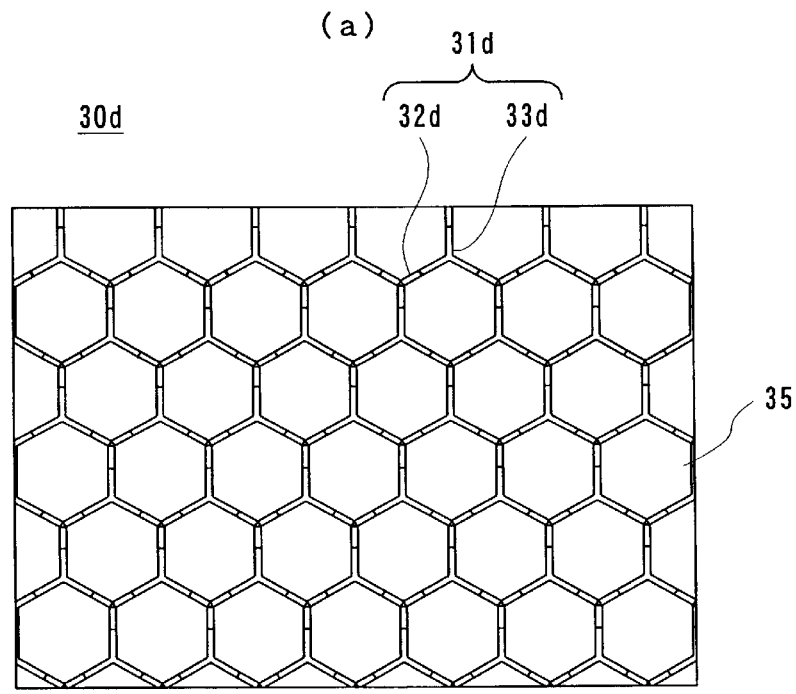
FIG. 10(a), FIG. 10(b) and FIG. 10(c) are a schematic plan view, a schematic side view of yet another example of a spacer according to an Embodiment 4 of the present invention, and a schematic perspective view of a projecting portion of the spacer, respectively.
Figure 10:
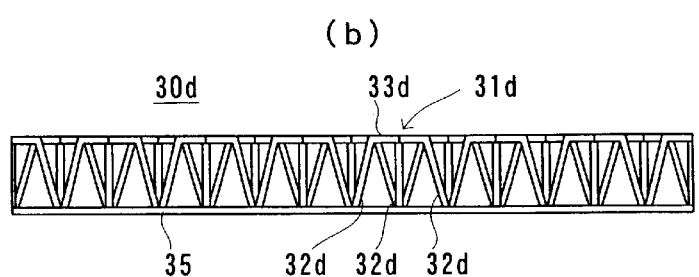
Figure 10:
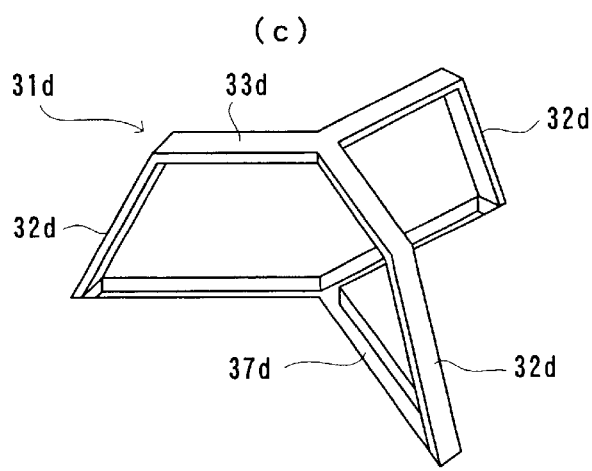
Figure 11:
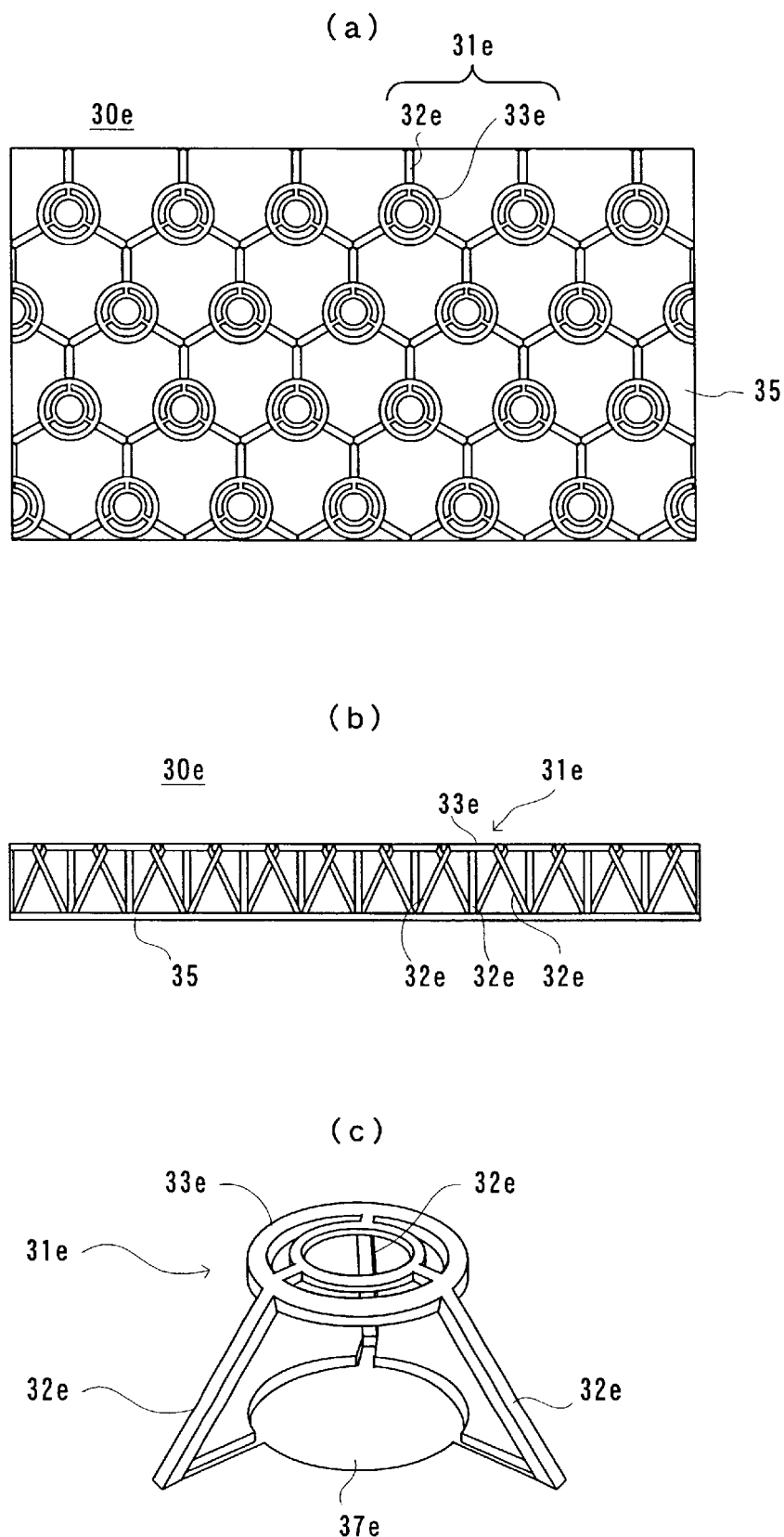
FIG. 11(a), FIG. 11(b) and FIG. 11(c) are a schematic plan view, a schematic side view of yet another example of a spacer according to an Embodiment 4 of the present invention, and a schematic perspective view of a projecting portion of the spacer, respectively.

Those member-connection type spacers 30c, 30d, 30e shown in FIG. 9, FIG. 10 and FIG. 11 are modified embodiments of the spacer 30b of FIG. 8, such that mainly the shape of the connecting member is modified in each of them. In the member-connection type spacer 30c of FIG. 9, each projecting portion 31c comprises three column-shaped members 32c and a connecting member 33c which is an equilateral triangle shaped frame. Each column-shaped member 32c has its tip end connected to one of the corners of the connecting member 33c. Further, in the member-connection type spacer 30d of FIG. 10, each projecting portion 31d comprises three column-shaped members 32d and a connecting member 33d which has an inverted "Y" shape. Each column-shaped member 32d has its tip end connected to one of the tip ends of the connecting member 33d. In the member-connection type spacer 30e of FIG. 11, each projecting portion 31e comprises three column-shaped members 32e and a connecting member 33e which has a double-circle ring shape. In each of spacers 30c, 30d, 30e, the other structure is substantially the same as the spacer 30b of FIG. 8.

Figure 12:
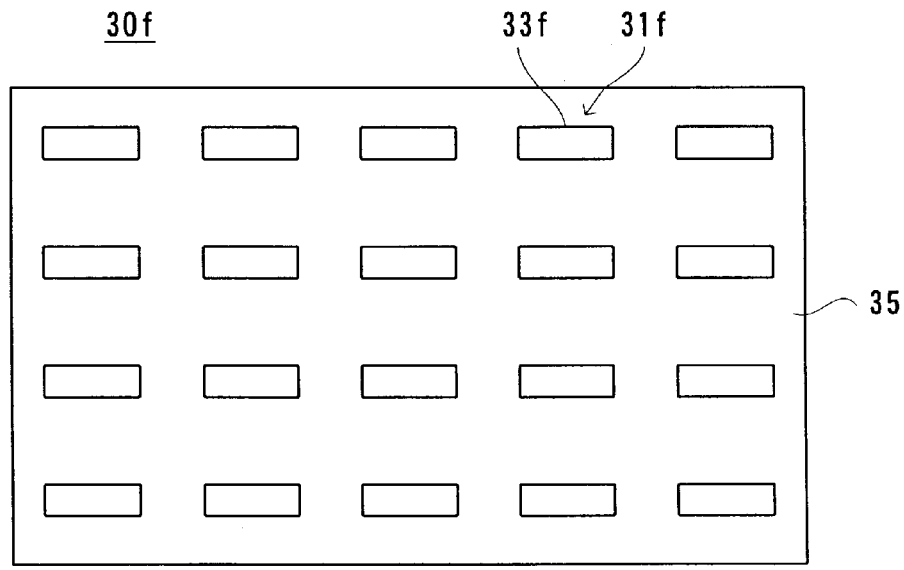
FIG. 12(a), FIG. 12(b) and FIG. 12(c) are a schematic plan view, a schematic side view of yet another example of a spacer according to an Embodiment 4 of the present invention, and a schematic perspective view of a projecting portion of the spacer, respectively.
Figure 12:
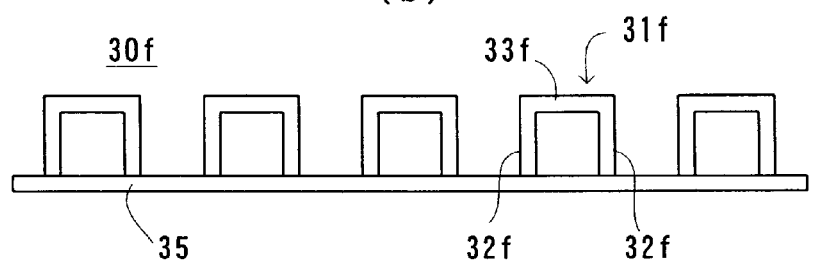
Figure 12:
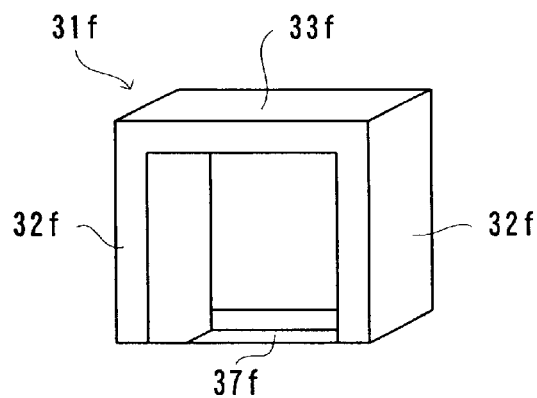

FIG. 12 shows a member-connection type spacer 30f including a plurality of projecting portions 31f which are arranged to be substantially flat on a rectangular base member 35. The projecting portions 31f are physically joined to be continuous via base member 35. As shown in FIG. 12(c), each projecting portion 31f comprises two column-shaped members 32f and a rod-like connecting member 33f. Each column-shaped member 32f is drawn vertically upwardly from the base member 35. Each column-shaped member 32f has its tip end connected to one of the tip ends of the connecting member 33f. The projecting portions 31b are regularly arranged at predetermined intervals such that the longitudinal direction of each projecting portion 31f is directed laterally.

Figure 13:
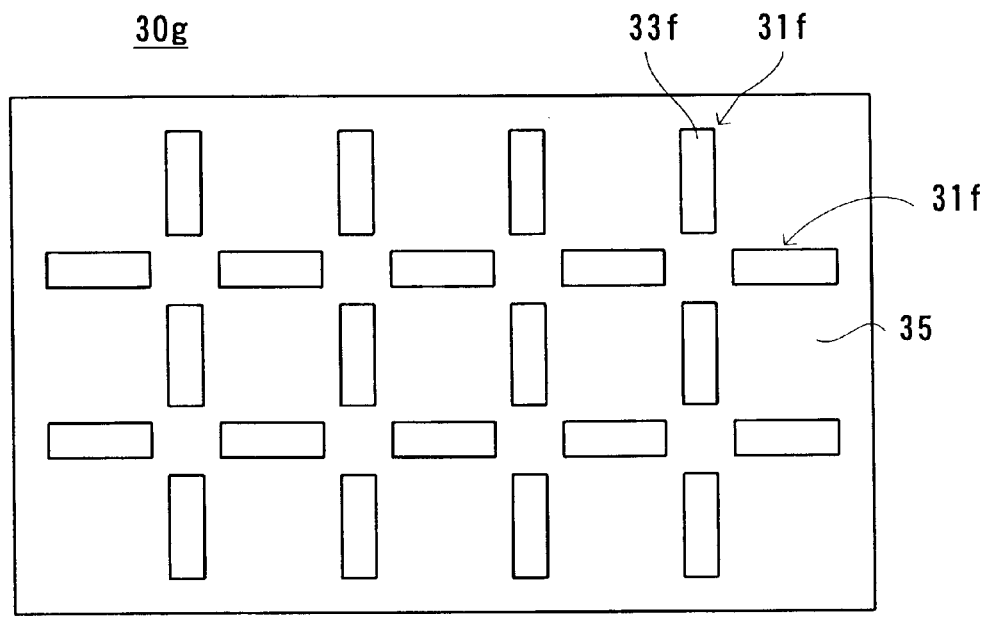
FIG. 13(a) and FIG. 13(b) are a schematic plan view, and a schematic side view of yet another example of a spacer according to an Embodiment 4 of the present invention, respectively.
Figure 13:
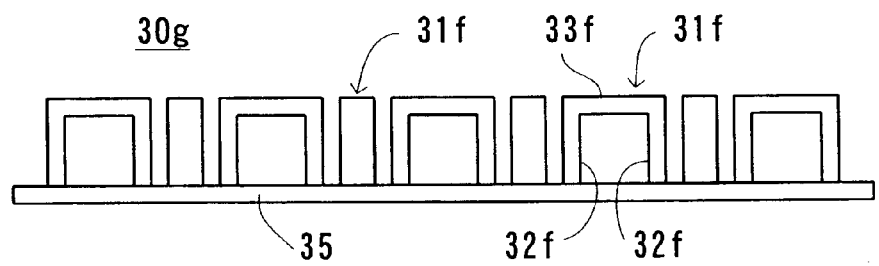

The member-connection type spacer 30g shown in FIG. 13 is a modified embodiment of the spacer 30f shown in FIG. 12, such that only the way to arrange the projecting portions 31f is modified. Namely, there are regularly and alternately arranged projecting portions 31f having the longitudinal directions thereof directed laterally, and projecting portions 31f having the longitudinal directions thereof directed longitudinally. Thus, the plurality of projecting portions 31f are arranged in a substantially square-meshed pattern when viewed from above. Other structure is substantially the same as the spacer 30f of FIG. 12.

Figure 14:
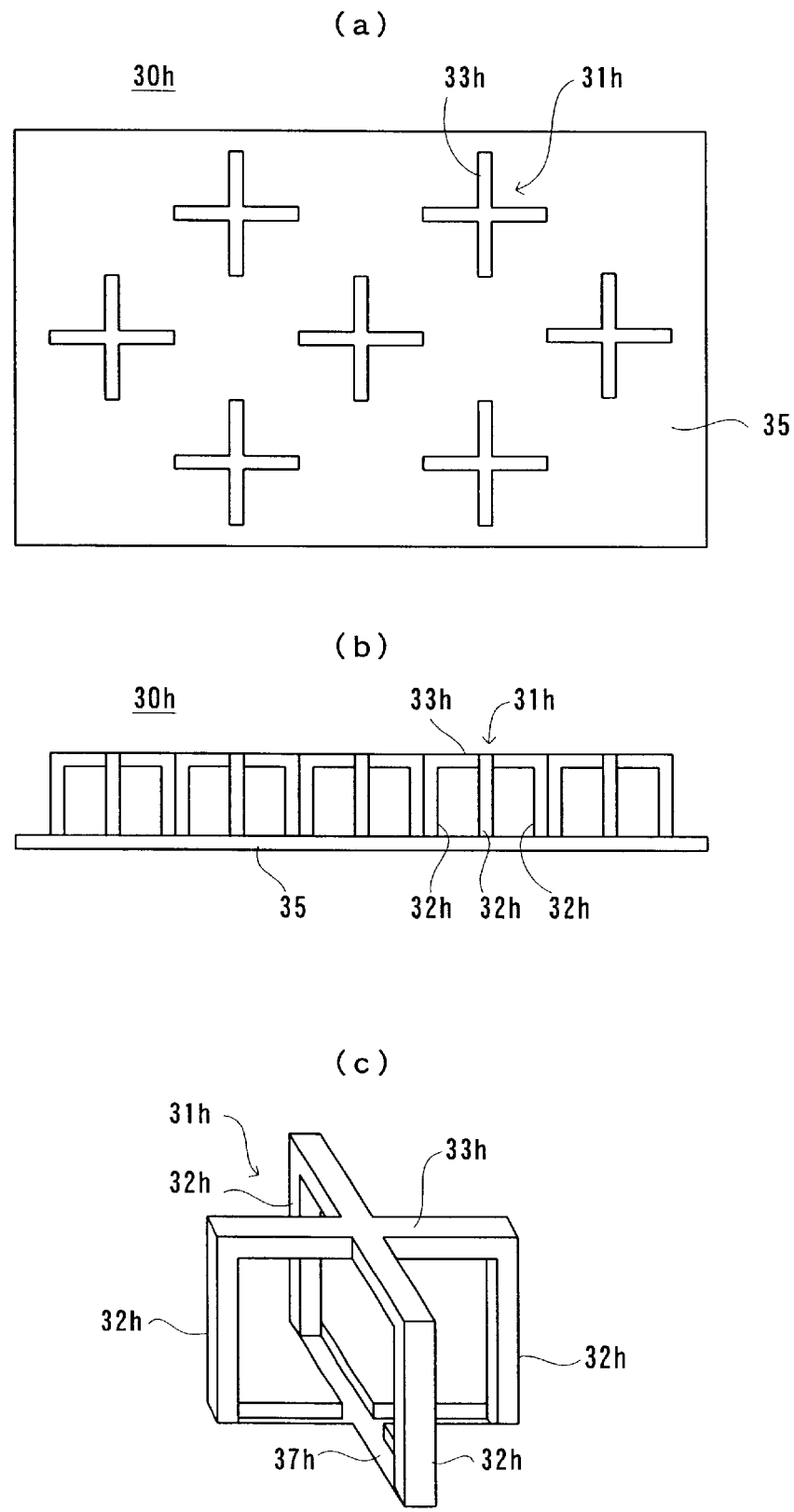
FIG. 14(a), FIG. 14(b) and FIG. 14(c) are a schematic plan view, a schematic side view of yet another example of a spacer according to an Embodiment 4 of the present invention, and a schematic perspective view of a projecting portion of the spacer, respectively.

The member-connection type spacer 30h shown in FIG. 14 includes a plurality of projecting portions 31h substantially flatly arranged on a rectangular base member 35. The projecting portions 31h are physically joined to be continuous via base member 35. As shown in FIG. 14(c), each projecting portion 31h comprises four column-shaped members 32h and a cross-shaped connecting member 33h. Each column-shaped member 32h is drawn vertically upward from the base member 35. The tip end of each column-shaped member 32h is connected to one of tip ends of the connecting member 33h. Further, the projecting portions 31h are regularly arranged at predetermined intervals.

Figure 15:
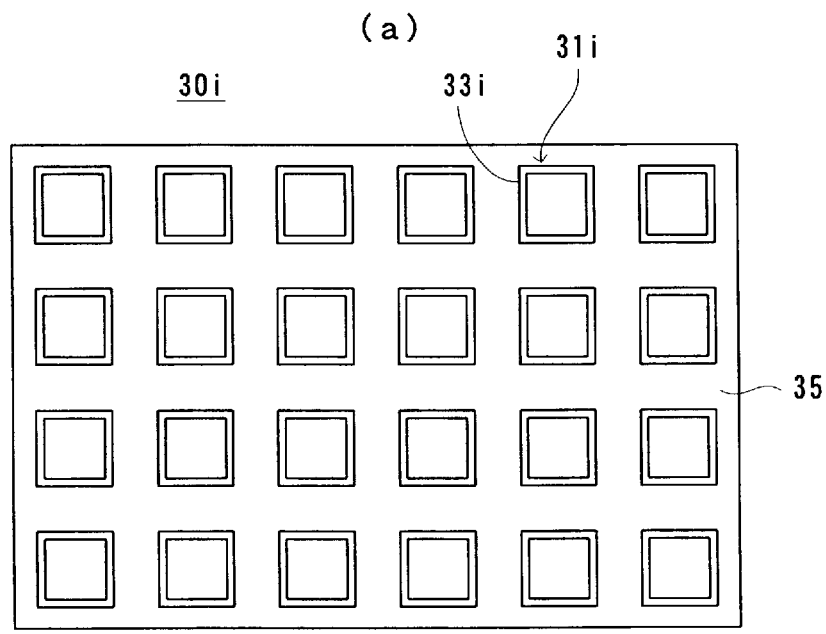
FIG. 15(a), FIG. 15(b) and FIG. 15(c) are a schematic plan view, a schematic side view of yet another example of a spacer according to an Embodiment 4 of the present invention, and a schematic perspective view of a projecting portion of the spacer, respectively.
Figure 15:
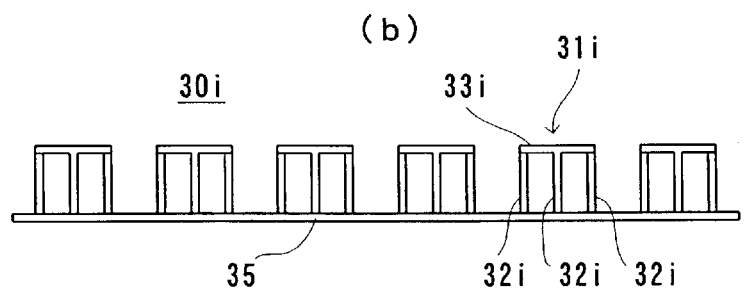
Figure 15:
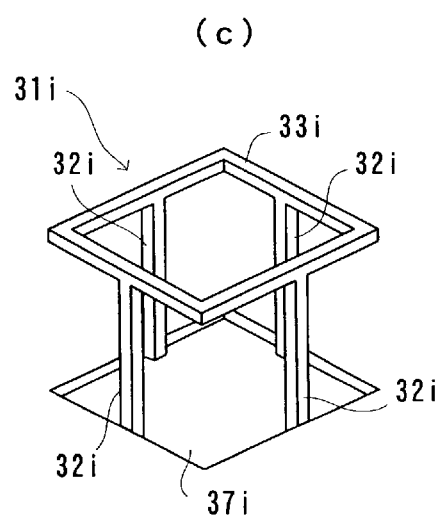

The member-connection type spacer 30i shown in FIG. 15 is a modified embodiment of the spacer 30h of FIG. 14, such that mainly the shape of the connecting member is modified. In the member-connection type spacer 30i of FIG. 15, each projecting portion 31i comprises three column-shaped members 32i and a connecting member 33i which is a square shaped frame. Each column-shaped member 32i has its tip end connected to a center portion of one side of the connecting member 33i. Other structure is substantially the same as the spacer 30h of FIG. 14.

In each of the aforementioned member-connection type spacers 30a, 30b, . . . , 30i, the width of each column-shaped member along the direction perpendicular to the gas-flowing direction is set at 0.2 mm to 1 cm when viewed from the thickness direction of the spacer. Further, the distance between column-shaped members themselves is set at 2 mm to 30 mm, for example. Thus, the number of column-shaped members per 1 $cm^2$ is 0.1 to 25 when viewed from the thickness direction of the spacer. This is also true in an Embodiment 5 to be described hereinafter.

Further, each of member-connection type spacers 30a, 30b, . . . , 30i is integrally formed such as by injection molding of soft plastics. Thus, the column-shaped members and accompanying connecting members are continuous in a seamless manner as a matter of course, and some of the column-shaped members continuously and smoothly transfer to the connecting member depending on the shapes of the column-shaped members and connecting members. By virtue of such integral formation, none of the member-connection type spacers 30a, 30b, . . . , 30i has portions which overlap with other portions of the spacer via space in the thickness direction of the spacer. Thus, in each of the member-connection type spacers 30a, 30b, . . . , 30i shown in (c) of FIG. 7 through FIG. 15, there is formed a predetermined hole 37a, 37b, . . . , 37i such as at those areas of the base member, which are opposed to the column-shaped members drawn obliquely upwardly from the base member and which are opposed to the connecting member.

Each member-connection type spacer of the Embodiment 4 has a first feature of reduced degree of rugged feeling, since the spacer has a large number of connecting members per a unit area when viewed from the thickness direction of the spacer. Further, each spacer has increased flexibility and is capable of bearing a heavier load, considering the light weight of the spacer. Moreover, each spacer can be used for any type of cooling device, since the projecting portions of the spacer can be formed in various shapes. For example, the spacer 30a having the square framed connecting members shown in FIG. 7 is capable of bearing a considerably heavy load, by increasing the thickness. Thus, the spacer can be used for a cooling device such as an underlying futon. Conversely, reducing the thickness extremely reduces the weight and improves the flexibility, to thereby allow the spacer to be used for a cooling device such as clothes. In this way, the member-connection type spacers have versatility.

Note, in case of increasing the strength of each member-connection type spacer of the Embodiment 4, it is enough, for example, to mutually connect adjacent column-shaped members themselves or adjacent connecting members themselves by another connecting member, concerning some of the plurality of projecting portions.

Embodiment 5

FIG. 16(a), FIG. 16(b) and FIG. 16(c) are a schematic partial plan view, a schematic partial side view and a schematic partial perspective view of a cooling device aimed spacer 40 of the Embodiment 5, respectively.

Figure 16:
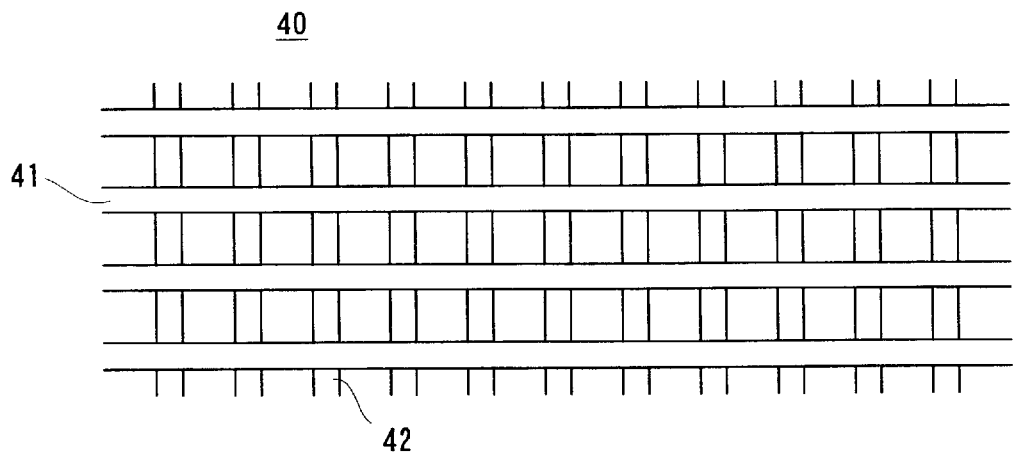
FIG. 16(a), FIG. 16(b) and FIG. 16(c) are a schematic partial plan view, a schematic partial side view and a schematic partial perspective view of a spacer according to an Embodiment 5 of the present invention, respectively.
Figure 16:
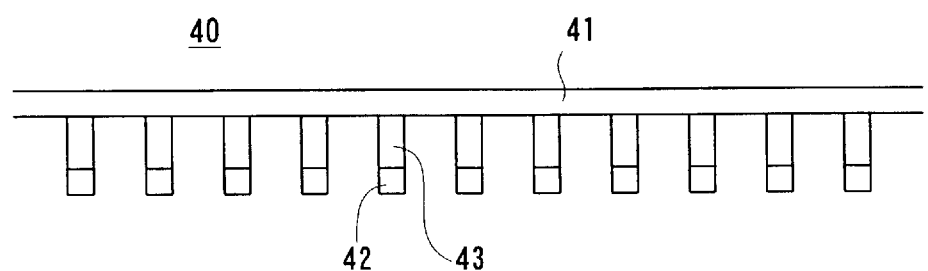
Figure 16:
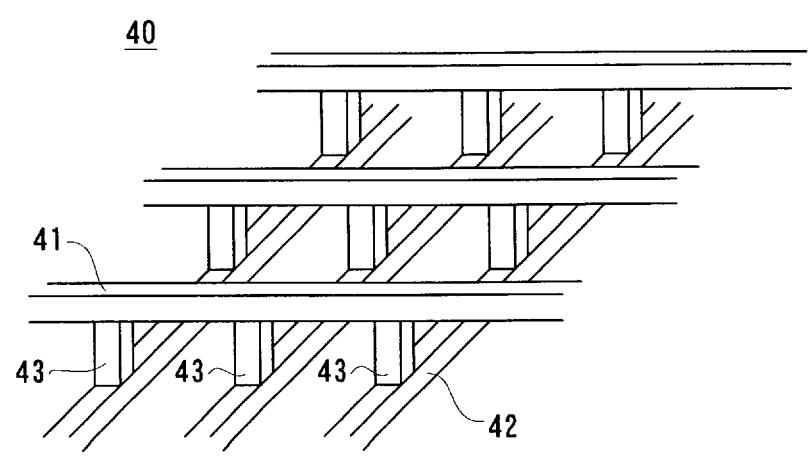

The cooling device aimed spacer 40 shown in FIG. 16 is called an "upper and lower line type", which includes a plurality of upper rails 41, a plurality of lower rails 42 and a plurality of column-shaped members 43. The plurality of upper rails 41 are arranged at predetermined intervals in the vertical direction in FIG. 16(*a*), while the plurality of lower rails 42 are arranged at predetermined intervals in the lateral direction in FIG. 16(*a*). The column-shaped members 43 are provided at those intersections between upper rails 41 and lower rails 42 when viewed from above, respectively, so as to interconnect the upper rails 41 and lower rails 42. Thus, the plurality of column-shaped members 43 are physically joined to be continuous via upper rails 41 and lower rails 42.

In the Embodiment 5, the upper rails 41 correspond to the connecting members in the present invention. In this case, it is assumed that one projecting portion is constituted of one upper rail 41 and the plurality of column-shaped members 43 connected by the upper rail 41.

The upper and lower line type spacer 40 can be formed such as by injection molding of plastics.

The spacer 40 of the Embodiment 5 has upper and lower meshed sides, so that the spacer 40 exhibits a lesser degree of a rugged feeling and is extremely lightweight with increased flexibility. The spacer 40 has a further feature that its function is unchanged even when it is inverted. Thus, in forming a cooling flow passage in a cooling device, the spacer 40 can be used invertedly. When an increased strength is required for the spacer 40, the column-shaped members 43 may be thickened.

Further, larger pushing forces against the spacer 40 of the Embodiment 5 may widen the distance between upper rails or between the lower rails. To avoid such a situation, it is possible to provide connecting members for mutually connecting adjacent upper rails or adjacent lower rails at several points.

Meanwhile, in those spacers of the aforementioned Embodiments 1 through 4, it is desirable to form a lot of large holes in the base members, as required. Namely, those spacers having the plurality of projecting portions arranged on the respective base members shall be used to set the respective base members downwardly and to place the user's body on the upper ends of the projecting portions, in case of applying the respective spacers to cooling devices. However, it is certain that a cooling seat cushion is used invertedly. As such, forming large holes in the base member reduces that area of the spacer which contacts with the user's body, to thereby allow to use the cooling seat cushion invertedly. Moreover, forming a large number of large holes in the base member further lightens the spacer to thereby advantageously increase the flexibility of the spacer.

In addition, there exist the following methods to obtain a larger spacer such as in a size of 2 m×2 m from those spacers made of small pieces as shown in Embodiments 1 through 4. Namely, it is possible to readily fabricate a larger spacer by mutually abutting sides of respective pieces and by heat welding them, when the material of the spacer is plastics. It is also possible to adhere the respective pieces onto a large plate, or to connect the respective pieces by connectors such that the respective pieces can be folded relative to one another.

There will be described hereinafter cooling devices applied with the cooling devices aimed spacers according to the present invention, respectively. Herein, there will be described situations where such cooling device aimed spacers are applied to an air flow-through type cooling seat cushion and a vaporization heat utilizing type cooling pillow, respectively.

Application Example to Cooling Seat Cushion

Figure 17:
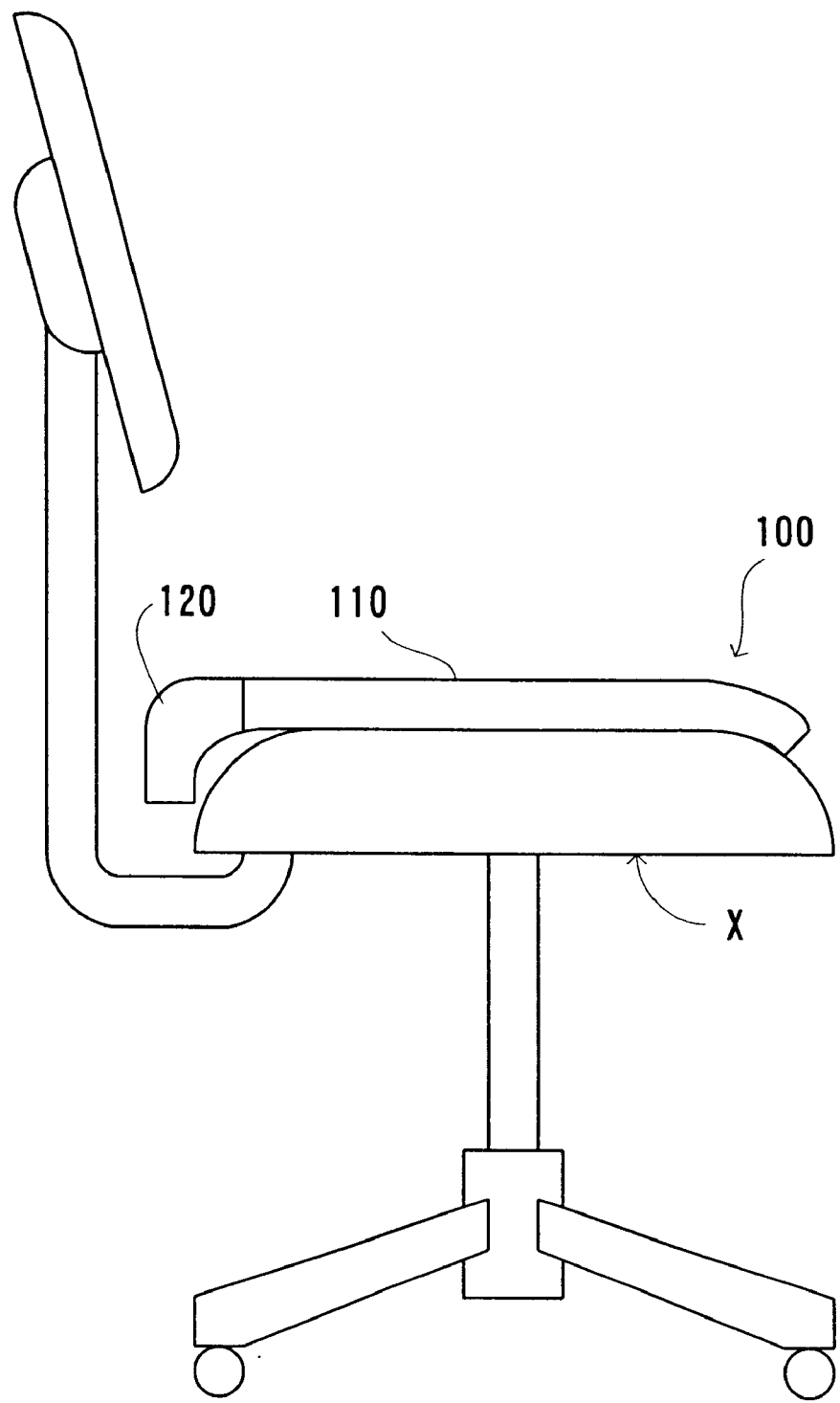
FIG. 17 is a view showing a situation where a cooling seat cushion applied with the spacer of the Embodiment 4 is placed on a chair.
Figure 18:
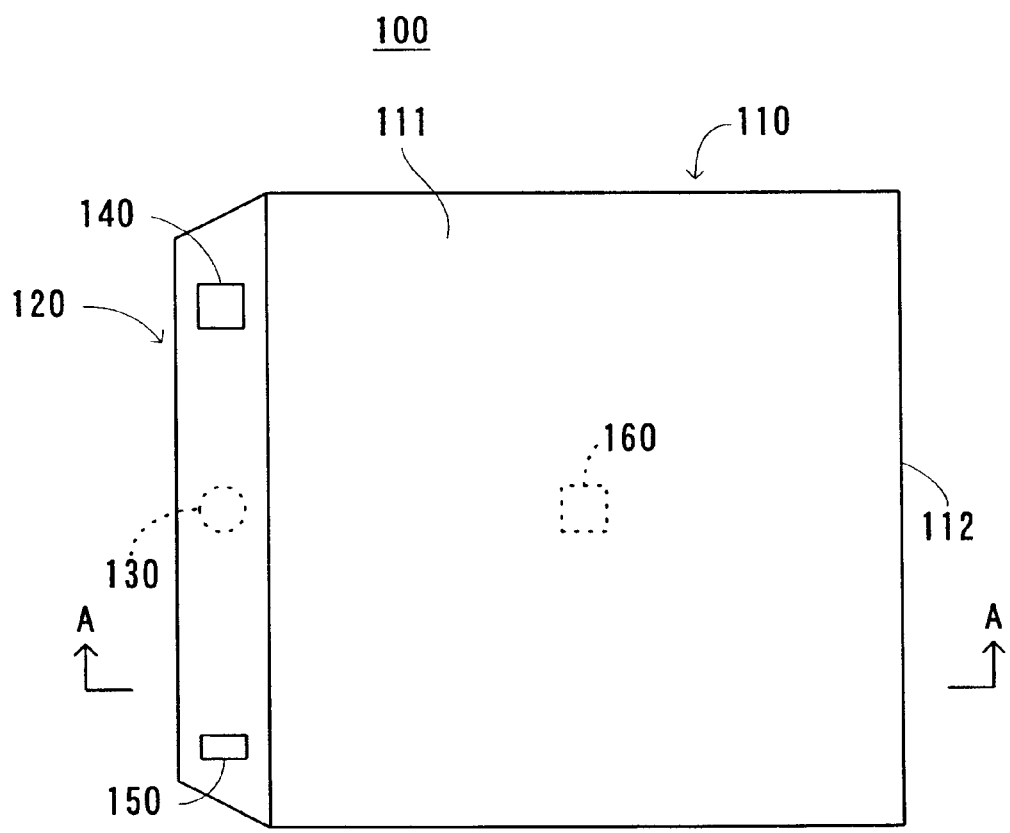
FIG. 18(a) and FIG. 18(b) are a schematic plan view and a schematic cross-sectional view of the cooling seat cushion of FIG. 17, respectively.
Figure 18:
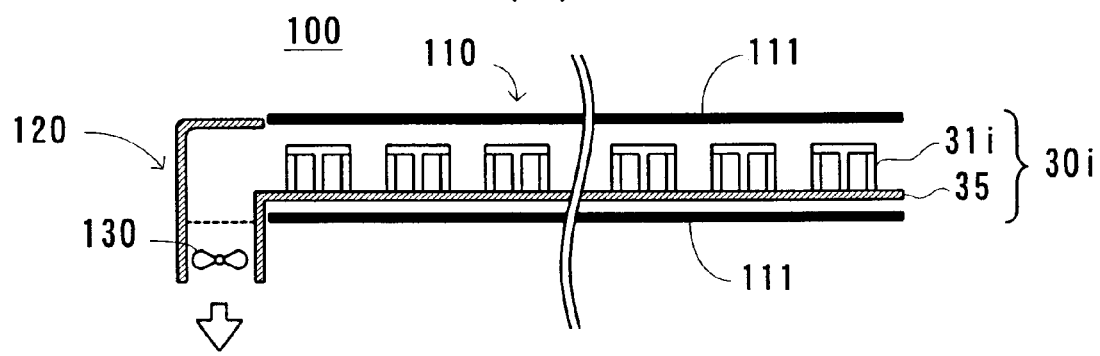

FIG. 17 is a view showing a situation where a cooling seat cushion applied with the cooling device aimed spacer of the present invention is placed on a chair, FIG. 18(*a*) is a schematic plan view of the cooling seat cushion, and FIG. 18(*b*) is a schematic cross-sectional view of the cooling seat cushion viewed in an A—A arrow direction.

As shown in FIG. 17, such a cooling seat cushion 100 is used by placing it on a chair X. It is of course possible to use it by placing it such as on a bench or sofa. As shown in FIG. 18, this cooling seat cushion 100 includes a cooling flow passage 110, a connecting flow passage 120, a DC fan 130 as a blowing means, a battery 140, a main switch 150 and a pressure switch 160. The cooling flow passage 110 is provided for flowing air by the DC fan 130, and comprises a square spacer 30*i* of a size of 400 mm×400 mm and a sheet 111. Namely, this example adopts the member-connection type spacer 30*i* shown in FIG. 15. Considering that the cooling seat cushion 100 is used by placing it on the chair, the whole size of the cooling seat cushion 100 is desirably of a size on the order of 500 mm×500 mm at the utmost.

The sheet 111 is formed in a sack shape to cover the whole of the spacer 30*i*. Note, the sheet 111 has a right side 112 opened to suck air, in FIG. 18(*a*). The material of the sheet 111 may be whatever readily allows water vapor to permeate therethrough, such as high-density cotton cloth, or typical cloth.

The connecting flow passage 120 is a space provided between the DC fan 130 and the cooling flow passage 110. The DC fan 130 is provided to suck air from the cooling flow passage 110 and the connecting flow passage 120, and to discharge the air to the exterior. The battery 140 is to drive the DC fan 130. Such a battery 140 may be a normal dry cell, and preferably a rechargeable secondary cell which can be charged by a mains-power during disuse of the cooling seat cushion 100.

The pressure switch 160 is provided at a substantially central upper portion of the cooling flow passage 110. The main switch 150 and the pressure switch 160 are serially connected to each other, so that the DC fan 130 is supplied with power from the battery 140 when both switches 150, 160 are turned ON.

In use as shown in FIG. 17, the cooling seat cushion is placed such that the connecting flow passage 120 comes to the rear portion (backrest side) of the chair. The DC fan 130 is typically placed to set its blow opening downwardly, but may be inverted depending on the structure of the chair. When a user sits on the chair X under this condition, the pressure switch 160 is turned ON by sensing the sitting. If the main switch 150 has been kept ON, the DC fan 130 is rotated in a direction to suck ambient air from the right side 112 of the sheet 111. The air sucked via side 112 flows through the connecting flow passage 111 formed by the spacer 30*i*, and then discharged downwardly by the DC fan 130. It is enough that the amount of flowing air is on the order of 1 liter/sec, so that the DC fan 130 for flowing such an amount of air is of a small size of 40 mm length×40 mm width×10 mm thickness.

Such a cooling seat cushion is capable of increasing the temperature gradient at the hips of a user who has sat on the cooling seat cushion, by causing ambient air cooler than the user's body temperature to flow just under the hips. Thus, sitting for a long time causes no increase of the temperature of those portions of the cooling seat cushion which contact with hips because of the user's body temperature, to thereby prevent a sweaty condition and to thereby provide a comfortable feeling.

Providing a lot of large holes at the base member 35 of the spacer 30*i* allows a sufficient cooling effect to be obtained even when the cooling seat cushion is used invertedly. Also in this case, it is possible to prevent a sweaty condition.

Application Example to Cooling Pillow

Figure 20:
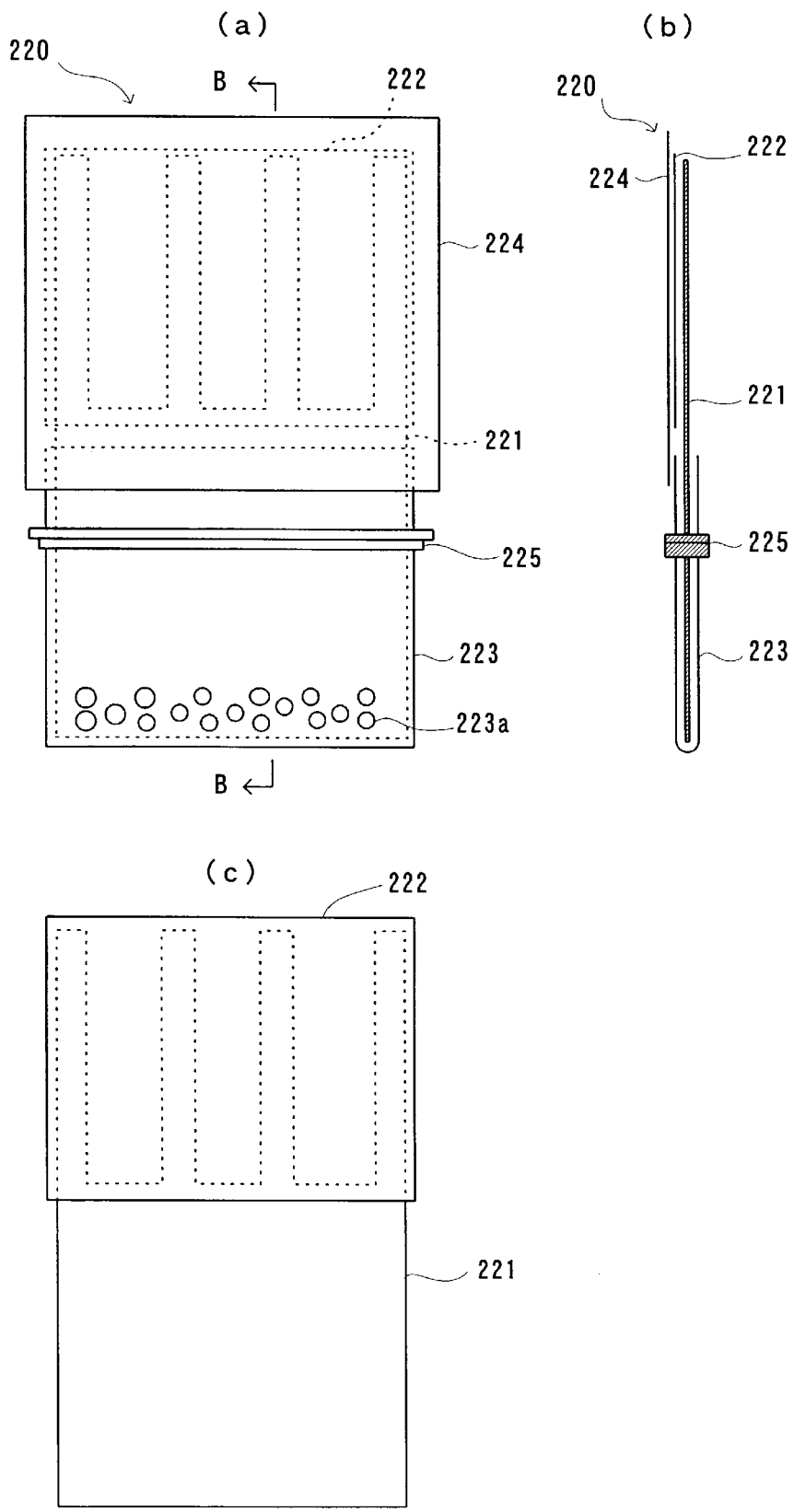
FIG. 20(a), FIG. 20(b) and FIG. 20(c) are a schematic plan view, a schematic cross-sectional view of an evaporation sheet to be used for the cooling pillow of FIG. 19, and a schematic plan view of a water conducting cloth and a thin cloth cooperatively constituting the evaporation sheet, respectively.
Figure 21:
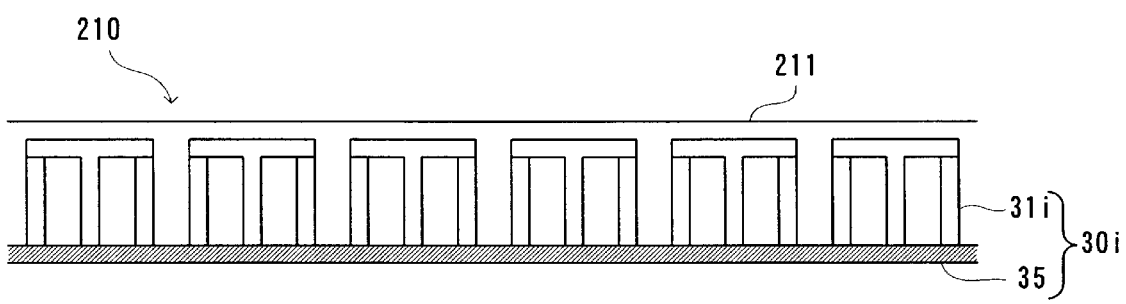
FIG. 21 is a schematic partial cross-sectional view of an air flow passage of the cooling pillow of FIG. 19.

FIG. 19(a), FIG. 19(b) and FIG. 19(c) are a schematic plan view, a schematic front view and a schematic right side view, respectively, of a cooling pillow applied with the spacer of the present invention. FIG. 20(a) is a schematic plan view of an evaporation sheet to be used for the cooling pillow, FIG. 20(b) is a schematic cross-sectional view of the evaporation sheet as viewed from a B—B arrow direction, and FIG. 20(c) is a schematic plan view of a water conducting cloth and a thin cloth constituting the evaporation sheet. Further, FIG. 21 is a schematic partial cross-sectional view of an air flow passage of the cooling pillow.

Figure 19:
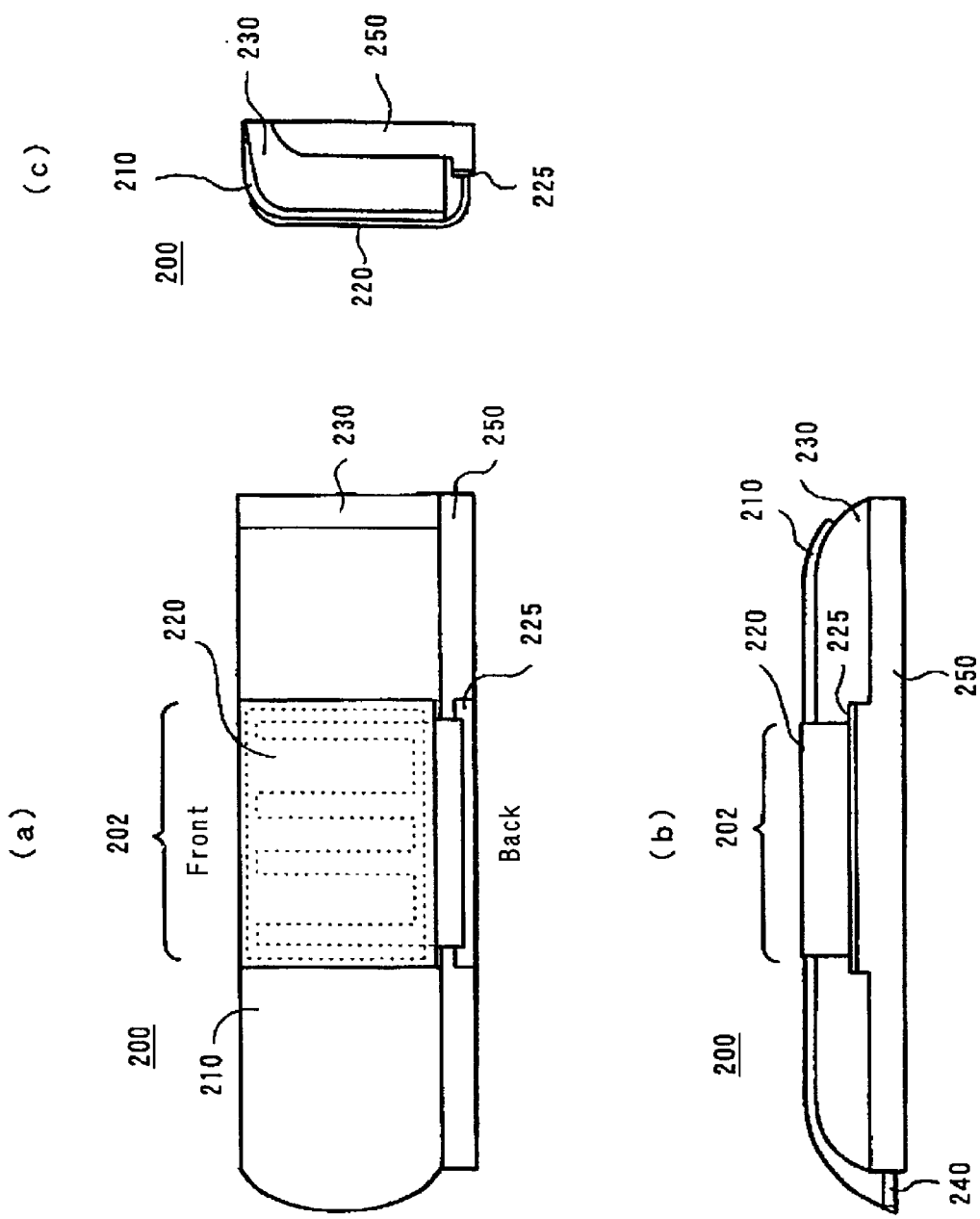
FIG. 19(a), FIG. 19(b) and FIG. 19(c) are a schematic plan view, a schematic front view and a schematic right side view, respectively, of a cooling pillow applied with the spacer of the Embodiment 4.

As shown in FIG. 19, the cooling pillow 200 is provided with an air flow passage 210, an evaporation sheet 220, a cushioning material 230, a fan 240 as blowing means, and a tank 250. The cooling pillow 200 has its center portion 202 for placing thereon a head of a sleeping user. The cooling pillow 200 has its lower portion provided with the tank 250 that is filled with water, and the cushioning material 230 is placed on the tank 250. The cushioning material 230 is provided for improving the feeling upon sleeping. In FIG. 19, the cooling pillow 200 is used such that the body of the sleeping user comes to the side labeled "Front".

The air flow passage 210 is placed on the cushioning material 230. Placed at the upper portion of the center portion 202 of the air flow passage 210 is an upper end portion of the evaporation sheet 220, and the other end portion of the evaporation sheet 220 is inserted into the tank 250 via a slit provided at the tank 250 and immersed in water therein.

As shown in FIG. 19(b), the air flow passage 210 is the passage through which the air flows, that is fed by the fan 240 provided at the side portion of the cooling pillow 200. The air passed through the air flow passage 210 is discharged to the exterior via the side portion (right side in FIG. 19(b)) opposite to the fan 240.

There will be now described the evaporation sheet 220. As shown in FIG. 20, the evaporation sheet 220 includes: a water conducting cloth 221 and a thin cloth 222, as a water conducting member; a water conducting cloth cover 223; a waterproof sheet 224 as a waterproof member; and a connector 225. As shown in FIG. 20(c), the upper portion of the water conducting cloth 221 is formed into a comb shape. This portion is adhered with the thin cloth 222 for allowing water to sufficiently permeate therethrough. For example, a towel cloth is adopted as the water conducting cloth 221. The towel cloth has a superior function to suck up water and to keep it.

As shown in FIG. 20(a) and FIG. 20(b), the lower portion of the water conducting cloth 221 is covered by the water conducting cloth cover 223 made of polyethylene. Further, the water conducting cloth cover 223 has its lower end formed with a lot of water suck holes 223a.

The lower portion of the water conducting cloth 221 covered by the water conducting cloth cover 223 is inserted into the connector 225. The connector 225 is removably inserted into the slit of the tank 250, to thereby facilitate insertion of the water conducting cloth 221 into the tank 250. Inserting the lower portion of the water conducting cloth 221 covered by the water conducting cloth cover 223 into the tank 250 causes the water conducting cloth 221 to suck up water via water suck holes 223a toward the upper portion of the water conducting cloth 221 by a capillary phenomenon.

The water conducting cloth cover 223 acts to prevent unnecessary evaporation of water upon sucking it up and to prevent the cushioning material 230 from being wetted.

As shown in FIG. 19(a), the thin cloth 222 and the comb shaped portion of the water conducting cloth 221 are placed on the center portion 202 of the air flow passage 210. The water sucked up from the lower portion of the water conducting cloth 221 is transferred to the thin cloth 222 from the comb shaped portion at the upper portion of the water conducting cloth 221, and is immediately dispersed to thereby spread over the thin cloth 222. Typically, the thin cloth 222 is wholly wetted in about 10 minutes after the lower end of the water conducting cloth 221 has been inserted into the tank 250. The comb shaped portion of the water conducting cloth. 221 and the thin cloth 222 both placed on the air flow passage 210 are further covered by the waterproof sheet 224 so as to prevent a user's head placed thereon from being wetted.

Note, the water conducting cloth 221, thin cloth 222 and waterproof sheet 224 may be individual members to be combined with one another, as already described above, or may be previously formed into an integral member.

As shown in FIG. 21, the air flow passage 210 includes the spacer 30i and a sheet 211. Namely, this embodiment adopts the member-connection type spacer 30i shown in FIG. 15. The whole spacer 30i, except for the center portion 202 of the air flow passage 210, is covered with the sheet 211 from the upper side of the spacer 30i. For example, a high-density cotton cloth is adopted as the sheet 211. On the other hand, placed on the center portion 202 of the air flow passage 210 is the evaporation sheet 220 with the waterproof sheet 224 kept at the upper side. Thus, the air flowing through the center portion 202 of the air flow passage 210 closely contacts with the thin cloth 222.

There will be now explained a principle where the cooling pillow 200 cools a user's head.

As described above, the cooling pillow 200 is provided at its side portion with the fan 240. This fan 240 takes in air from the underside and feeds the air to the above. This air is flown through the air flow passage 210 provided on the cushioning material 230, and discharged to the exterior from the side portion opposite to the side where the fan 240 is provided. At this time, the air flowing through the center portion 202 of the air flow passage 210 closely contacts with the thin cloth 222. By the contact of the air with the thin cloth 222, the water content held in the thin cloth 222 is promoted to evaporate. The evaporated water content is taken away to the exterior together with the flowing air. Water takes away a vaporization heat from surrounding water molecules upon evaporating into a gas state, so that the temperature of the water held in the thin cloth 222 is lowered. Thus, the user's head contacting with the thin cloth 222 via waterproof sheet 224 is cooled so that the sleeping user feels coolness at the head.

Further, the water content within the evaporation sheet 220 having been cooled upon evaporation closely contacts with the air flowing through the air flow passage 210 to thereby also cool this air. Namely, the endothermic effect by virtue of evaporation of water serves in two forms to cool the evaporation sheet 220 and to cool the air within the air flow passage 210. Cooling the air within the air flow passage 210 extremely increases the temperature gradient near the user's head, since the position of the air flow passage 210 is extremely close to the user's head. The thus increased temperature gradient promotes heat radiation, to thereby cause the user to feel more coolness.

As explained above, the cooling device aimed spacers according to the present invention are capable of reducing the viscous drag upon impingement of flowing air onto projecting portions, to thereby allow to flow a lot of air even by a lower pressure. Thus, such cooling device aimed spacers are preferably used for cooling devices such as cooling bedclothes, cooling seat cushions, cooling mats, cooling chairs, cooling clothes, and cooling shoes, for flowing air parallel near a user's body surface to thereby cool the user's body.

Note, the present invention is not limited to the aforementioned embodiments, and can be variously modified within the scope of the gist of the invention.

For example, those cooling device aimed spacers shown in FIGS. 3 through 15 have been described about a situation where the plurality of projecting portions have been formed at the upper surfaces of the base members, respectively. However, the projecting portions may be formed on both of the upper and lower surfaces of the base members, respectively.

INDUSTRIAL APPLICABILITY

As explained above, the cooling device aimed spacers according to the present invention are capable of reducing the viscous drag upon impingement of flowing air onto projecting portions, to thereby allow to flow a lot of air even by a lower pressure. Thus, such cooling device aimed spacers can be used for cooling devices such as cooling bedclothes, cooling seat cushions, cooling mats, cooling chairs, cooling clothes, and cooling shoes, for flowing air parallel near the user's body surface to thereby cool the user's body.

What is claimed is:

1. A cooling device, comprising:
    a substantially flat flow passage formed at a side of the cooling device which contacts a human body;
    a blowing means for causing ambient air to flow through the flow passage to thereby increase a temperature gradient between the human body and the flow passage so as to cool the human body, with moisture due to perspiration from the human body being discharged into the flow passage;
    a cooling device aimed spacer forming the flow passage, said spacer comprising:
        a plurality of projecting portions arranged in a state where said projecting portions are upstanding in a thickness direction of the flow passage,
        said plurality of projecting portions being integrally formed of plastics to be physically continuous, each of said plurality of projecting portions having a width along a direction perpendicular to an air-flowing direction, the width being between 0.1 mm and 2 cm when viewed from the thickness direction of the flow passage, said plurality of projecting portions having an opening ratio within a plane perpendicular to the air-flowing direction of at least 30%, and an opening ratio at the side of the cooling device aimed spacer which contacts with the human body of at least 20%; and
        a meshed member provided on said plurality of projecting portions.

2. A cooling device aimed spacer to be used in a cooling device which cools a cooling object by a flow of a gas through a substantially flat flow passage formed at that side of the cooling device which contacts with the cooling object, in which said cooling device aimed spacer serves to form flow passage and comprises:
    a plurality of column-shaped members each having a length component in the thickness direction of the flow passage, and a plurality of connecting members for connecting one ends of the plurality of column-shaped members,
    wherein said plurality of column-shaped members and said plurality of connecting members are integrally formed of plastics to become physically continuous such that: the width of each of said column-shaped members along a direction perpendicular to the gas-flowing direction is in a range of 0.2 mm to 1 cm when viewed form the thickness direction of the flow passage; and said column-shaped members are formed at a ration of 0.1 to 25 pieces for 1 cm$^2$ when viewed form the thickness direction of the flow passage.

3. A cooling device aimed spacer of claim 2,
    wherein said plurality of column-shaped members and said plurality of connecting members are free of overlapping with other members of said spacer via space along the thickness direction of the flow passage.

4. A cooling device aimed spacer of claim 2, further comprising:
    a meshed member provided on said plurality of connecting members.

5. A cooling device aimed spacer to be used in a cooling device, and being adapted to form a substantially flat flow passage through which ambient air can flow, and comprising:
    a plurality of projecting portions arranged in a state where said projecting portions are upstanding in a thickness direction of the flow passage, said plurality of projecting portions being integrally formed of plastics to be physically continuous, each of said plurality of projecting portions having a width along a direction perpendicular to an air-flowing direction, the width being 0.1 mm and 2 cm when viewed from the thickness direction of the flow passage, said plurality of projecting portions having an opening ratio within a plane perpendicular to the air-flowing direction of at least 30%, and an opening ratio at a side of the cooling device aimed spacer which is contactable with the human body of the at least 20%, said projects being configured to increase a temperature gradient between the human body and the flow passage so as to cool the human body, with moisture due to perspiration from the human body being dischargeable into the flow passage.

* * * * *